United States Patent
Stimson

(10) Patent No.: US 11,267,860 B2
(45) Date of Patent: *Mar. 8, 2022

(54) COMPOSITIONS AND METHODS RELATING TO THE TREATMENT OF DISEASES

(71) Applicant: ILC THERAPEUTICS LTD, Lanarkshire (GB)

(72) Inventor: William Stimson, Glasgow (GB)

(73) Assignee: ILC Therapeutics, LTD, Lanarkshire (GB)

( * ) Notice: Subject to any disclaimer, the term of this patent is extended or adjusted under 35 U.S.C. 154(b) by 386 days.

This patent is subject to a terminal disclaimer.

(21) Appl. No.: 15/760,200

(22) PCT Filed: Sep. 14, 2016

(86) PCT No.: PCT/GB2016/052841
§ 371 (c)(1),
(2) Date: Mar. 14, 2018

(87) PCT Pub. No.: WO2017/046583
PCT Pub. Date: Mar. 23, 2017

(65) Prior Publication Data
US 2018/0273597 A1    Sep. 27, 2018
US 2019/0144519 A9    May 16, 2019

(30) Foreign Application Priority Data

Sep. 15, 2015   (GB) ..................................... 1516303
Sep. 16, 2015   (GB) ..................................... 1516437

(51) Int. Cl.
| | |
|---|---|
| *A61K 38/21* | (2006.01) |
| *C07K 14/56* | (2006.01) |
| *C07K 19/00* | (2006.01) |
| *A61K 39/00* | (2006.01) |
| *A61K 39/35* | (2006.01) |

(52) U.S. Cl.
CPC ............ *C07K 14/56* (2013.01); *A61K 38/212* (2013.01); *A61K 39/0011* (2013.01); *A61K 39/35* (2013.01); *C07K 19/00* (2013.01); *C07K 2319/00* (2013.01)

(58) Field of Classification Search
CPC .................................................. A61K 38/212
See application file for complete search history.

(56) References Cited

U.S. PATENT DOCUMENTS 6,350,589 B1    2/2002    Morris et al.

FOREIGN PATENT DOCUMENTS

| WO | WO 1995/24212 A1 | 9/1995 |
| WO | WO 2014/037717 A1 | 3/2014 |
| WO | WO 2015/136287 A2 | 9/2015 |

OTHER PUBLICATIONS

Santhanam S., et al. Potential of interferon-alpha in solid tumors. Part 2. Biodrugs, 2002, 16(5):349-372.*
Crow, M.K., Interferon-alpha: a therapeutic target in systemic lupus erythematosus. Rheum. Dis. Clin. North Am., 2010, 36(1):173, pp. 1-13.*
Goldstein, D., et al. The role of interferon in cancer therapy: a current perspective. CA Cancer J. Clin., 1988, 38:258-277.*
Gonzalez-van Horn, S.R., et al. Interferon at the crossroads of allergy and viral infections. J. Leuk. Biol., 2015, 98:185-194.*
Kotredes, K.P., et al. The protective role of type I interferons in the gastrointestinal tract. Frontiers in Immunology, 2017, 8:410, pp. 1-10.*
Psarras, A., et al. Type I interferon-mediated autoimmune diseases: pathogenesis, diagnosis and targeted therapy. Rheumatology, 2017, 56:1662-1675.*
Mangodt, et al., "The role of Th17 and Treg responses in the pathogenesis of RSV infection," *Pediatric Research*, vol. 78, No. 5, pp. 483-491, (Nov. 2015).
PCT/GB2016/052841 International Search Report and Written Opinion dated Feb. 15, 2017.
Jin et al. "IL-17 cytokines in immunity and inflammation" Emerg Microbes Infect. Sep. 2013; 2(9): e60, published online Sep. 13, 2013.
Katayama "Anti-interleukin-17A and anti-interleukin-23 antibodies may be effective against Alzheimer's disease: Role of neutrophils in the pathogenesis" Brain Behav. Jan. 2020;10(1):e01504.
Kim et al. "Multi-cellular natural killer (NK) cell clusters enhance NK cell activation through localizing IL-2 within the cluster" Scientific Reports Jan. 11, 2017 7(40623).
Li et al. "Interleukin 17 receptor-based signaling and implications for disease" Nat. Immunol. 2019, 20 (12): 1594-1602.
Ge et al. "Biology of Interleukin-17 and Its Pathophysiological Significance in Sepsis" Frontiers in Immunology 2020 11:1558.
Bastid et al. "The Emerging Role of the IL-17B/IL-17RB Pathway in cancer" Front. Immunol. 2020 11:718.
Razi et al. "IL-17 and colorectal cancer: From carcinogenesis to treatment" Cytokine 2019 116:7-12—abstract.

(Continued)

*Primary Examiner* — Prema M Mertz
(74) *Attorney, Agent, or Firm* — Alston & Bird LLP

(57) ABSTRACT

The present invention relates to compositions and methods for promoting the induction of a cell-mediated immune response (such as that mediated by Th1 cells) and the suppression of a humoral or allergic immune response (such as that mediated by Th2 and Th17 cells). In particular, the invention relates to compositions and methods for preventing or treating allergy, such as food allergy, and associated allergic diseases, and conditions where an exaggerated Th17 response plays a detrimental role, such as inflammatory responses and autoimmune diseases. The invention further extends to the use of the compositions of the invention in the treatment and/or prophylaxis of allergy and associated allergic diseases and also of cancer.

12 Claims, 18 Drawing Sheets

Specification includes a Sequence Listing.

(56) References Cited

OTHER PUBLICATIONS

Fabregat et al. "TGF-beta signaling in cancer treatment" Curr Pharm Des. May 14, 2014; 20(17):2934-47—abstract.
Pai et al. "Wnt/beta-catenin pathway: modulating anticancer immune response" J Hematol Oncol May 5, 2017;10(1):101.

* cited by examiner

CDLPQTHSLGNRRALILLGQMGRISPFSCLKDRHDFRIPQEEFD
GNQFQKAQAISVLHEM

MQQTFNLFSTKNSSAAWDETLLEKFYIELFQQMNDLEACVIQEV
GVEETPLMNEDSILAV

KKYFQRITLYLIERKYSPCAWEVVRAEIMRSLSFSTNLQKRLRRK
D
(SEQ ID NO: 1)

Figure 9.

Reverse translation of the protein sequence of SEQ ID NO: 1 when an E. coli codon usage table is used.

ATGTGTGATCTGCCGCAGACCCATAGCCTGGGTAATCGTCGTGCACTGATTCTGCTGGGTCA
GATGGGTCGTATTAGCCCGTTTAGCTGTCTGAAAGATCGTCATGATTTTCGTATTCCGCAAG
AGGAATTTGATGGCAACCAGTTTCAGAAAGCACAGGCAATTAGCGTTCTGCATGAAATGATG
CAGCAGACCTTTAACCTGTTTAGCACCAAAAATAGCAGCGCAGCATGGGATGAAACCCTGCT
GGAAAAATTCTATATCGAACTGTTTCAGCAGATGAACGATCTGGAAGCATGTGTTATTCAAG
AAGTTGGCGTTGAAGAAACACCGCTGATGAATGAAGATAGCATTCTGGCAGTGAAAAAATAC
TTTCAGCGCATTACCCTGTATCTGATCGAACGTAAATATAGCCCGTGTGCATGGGAAGTTGT
TCGTGCAGAAATTATGCGTAGCCTGAGCTTTAGCACCAATCTGCAAAAACGTCTGCGTCGCA
AAGATTAATAA (SEQ ID NO: 2)

Figure 10.

SEQUENCE LISTING

<160> NUMBER OF SEQ ID NOS: 5

<210> SEQ ID NO 1
<211> LENGTH: 166
<212> TYPE: PRT
<213> ORGANISM: Homo sapiens

<400> SEQUENCE: 1

Cys Asp Leu Pro Gln Thr His Ser Leu Gly Asn Arg Arg Ala Leu Ile

```
1               5                   10                  15
Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
            35                  40                  45

Gln Lys Ala Gln Ala Ile Ser Val Leu His Glu Met Met Gln Gln Thr
            50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
                100                 105                 110

Asn Glu Asp Ser Ile Leu Ala Val Lys Lys Tyr Phe Gln Arg Ile Thr
                115                 120                 125

Leu Tyr Leu Ile Glu Arg Lys Tyr Ser Pro Cys Ala Trp Glu Val Val
            130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 2
<211> LENGTH: 507
<212> TYPE: DNA
<213> ORGANISM: Homo sapiens

<400> SEQUENCE: 2
atgtgtgatc tgccgcagac ccatagcctg ggtaatcgtc gtgcactgat tctgctgggt    60
cagatgggtc gtattagccc gtttagctgt ctgaaagatc gtcatgattt cgtattccg   120 caagaggaat tgatggcaa ccagtttcag aaagcacagg caattagcgt tctgcatgaa   180
atgatgcagc agacctttaa cctgtttagc accaaaaata gcagcgcagc atgggatgaa   240
accctgctgg aaaaattcta tatcgaactg tttcagcaga tgaacgatct ggaagcatgt   300
gttattcaag aagttggcgt tgaagaaaca ccgctgatga atgaagatag cattctggca   360
gtgaaaaaat actttcagcg cattaccctg tatctgatcg aacgtaaata tagcccgtgt   420
gcatgggaag ttgttcgtgc agaaattatg cgtagcctga gctttagcac caatctgcaa   480
aaacgtctgc gtcgcaaaga ttaataa                                       507

<210> SEQ ID NO 3
<211> LENGTH: 166
<212> TYPE: PRT
<213> ORGANISM: Homo sapiens

<400> SEQUENCE: 3

Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
            35                  40                  45

Gln Lys Ala Gln Ala Ile Ser Val Leu His Glu Met Met Gln Gln Thr
            50                  55                  60

Phe Asn Leu Phe Ser Thr Glu Asn Ser Ser Ala Ala Trp Glu Gln Thr
```

```
                        65                  70                  75                  80
Leu Leu Glu Lys Phe Ser Ile Glu Leu Phe Gln Gln Met Asn Asp Leu
                85                  90                  95

Glu Ala Cys Val Ile Gln Val Gly Val Glu Glu Thr Pro Leu Met
            100                 105                 110

Asn Glu Asp Ser Ile Leu Ala Val Arg Lys Tyr Phe Gln Arg Ile Thr
                115                 120                 125

Leu Tyr Leu Ile Glu Arg Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 4
<211> LENGTH: 189
<212> TYPE: PRT
<213> ORGANISM: Homo sapiens

<400> SEQUENCE: 4

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
                20                  25                  30

Gly Asn Arg Arg Ala Leu Ile Leu Leu Gly Gln Met Gly Arg Ile Ser
                35                  40                  45

Pro Phe Ser Cys Leu Lys Asp Arg His Asp Phe Arg Ile Pro Gln Glu
            50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
            115                 120                 125

Val Glu Glu Thr Pro Leu Met Asn Glu Asp Ser Ile Leu Ala Val Arg
130                 135                 140

Lys Tyr Phe Gln Arg Ile Thr Leu Tyr Leu Ile Glu Arg Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185

<210> SEQ ID NO 5
<211> LENGTH: 189
<212> TYPE: PRT
<213> ORGANISM: Homo sapiens

<400> SEQUENCE: 5

Met Ala Leu Pro Phe Ala Leu Met Met Ala Leu Val Val Leu Ser Cys
1               5                   10                  15

Lys Ser Ser Cys Ser Leu Gly Cys Asn Leu Ser Gln Thr His Ser Leu
                20                  25                  30

Asn Asn Arg Arg Thr Leu Met Leu Met Ala Gln Met Arg Arg Ile Ser
```

```
                35                  40                  45
Pro Phe Ser Cys Leu Lys Asp Arg His Asp Phe Glu Phe Pro Gln Glu
    50                  55                  60

Glu Phe Asp Gly Asn Gln Phe Gln Lys Ala Gln Ala Ile Ser Val Leu
65                  70                  75                  80

His Glu Met Met Gln Gln Thr Phe Asn Leu Phe Ser Thr Lys Asn Ser
                85                  90                  95

Ser Ala Ala Trp Asp Glu Thr Leu Leu Glu Lys Phe Tyr Ile Glu Leu
            100                 105                 110

Phe Gln Gln Met Asn Asp Leu Glu Ala Cys Val Ile Gln Glu Val Gly
            115                 120                 125

Val Glu Glu Thr Pro Leu Met Asn Glu Asp Ser Ile Leu Ala Val Lys
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser
            165                 170                 175

Phe Ser Thr Asn Leu Gln Lys Arg Leu Arg Arg Lys Asp
            180                 185
```

COMPOSITIONS AND METHODS RELATING TO THE TREATMENT OF DISEASES

CROSS REFERENCE TO RELATED APPLICATIONS

This application is a US national stage of PCT/GB2016/052841 filed Sep. 14, 2016, which claims priority from and the benefit of GB 1516303.3 filed Sep. 15, 2015 and GB 1516437.9 filed Sep. 16, 2015 all of which are incorporated herein by reference.

REFERENCE TO SEQUENCE LISTING

This application includes an electronic sequence listing in a file named 512158_SEQLST.txt, created on Mar. 14, 2018 and containing 13,868 bytes, which is hereby incorporated by reference in its entirety for all purposes.

FIELD OF THE INVENTION

The present invention relates to compositions and methods for promoting the induction of a cell-mediated immune response (such as that mediated by Th1 cells) and the suppression of a humoral or allergic immune response (such as that mediated by Th2 and Th17 cells). In particular, the invention relates to compositions and methods for preventing or treating allergy, such as food allergy, and associated allergic diseases, and conditions where an exaggerated Th17 response plays a detrimental role, such as inflammatory responses and autoimmune diseases. The invention further extends to the use of the compositions of the invention in the treatment and/or prophylaxis of allergy and associated allergic diseases and also of cancer.

BACKGROUND TO THE INVENTION

It is hypothesised that in certain circumstances, the Th1 response or the Th2/Th17 response can cause disease. An over-reactive Th1 response can generate organ-specific autoimmune disease such as arthritis, multiple sclerosis, or Type I diabetes, while an over-reactive Th2/Th17 response may underlie allergy and atrophy. It is currently believed that Th17 cells play a major role in host defence against pathogens and an exaggerated Th17 response may lead to severe inflammatory responses and autoimmune diseases—inflammatory bowel diseases (IBD), namely, ulcerative colitis (UC) and Crohn's disease (CD), are chronic inflammatory processes of the gastrointestinal tract. In these diseases a disturbed and exaggerated immune response, mainly towards the endogenous microflora, plays a major role. IL-17 expression is increased in both UC and CD. Type I IFNs have been studied in clinical trials in patients with UC and demonstrated efficacy in selected studies. As anti-viral cytokines, it is now known that Type I IFNs can regulate the development of Th17 cells.

It is known that different pathogens induce different IFN-α subtypes in vitro and that IFN-α subtypes have different antiviral, antiproliferative and immunomodulatory activities. Infection via a variety of routes, including orally, has been shown to induce different subtype profiles. IFN-α subtypes bind to the same receptor, activate common signaling pathways and are expected to have the same biological functions. All IFN-α subtypes have anti-viral activities, by definition, although their absolute efficacy in this context may vary considerably. In addition, many other biological properties have been described, but with varying potencies, including immunomodulatory and anti-proliferative activities. The pleiotropic effects appear to be due to differential interaction with the receptor chains and signaling through different intracellular pathways to an array of effector molecules. The Type I IFN receptor consists of two chains, IFNR1 and IFNR2. There is a range of binding affinities for each of the 12 IFN-α subtypes with the different receptor chains.

IFN-α may have a key role in the regulation of the Th1 response. It has been shown that IFN-α treatment promotes Th1 cell differentiation indirectly (largely via IFN-γ), but also appears to suppress Th2 cell development through the suppression of IL-4 and IL-13 gene expression. IFN-α therefore is able to re-establish a Th1/Th2 population balance in diseases and infections that promote a Th2 cell imbalance. In recent years, it became evident that besides its anti-viral effects, several immunomodulatory functions are exerted by IFN-α. IFN-α can impact on dendritic cell differentiation and controls the expression of various pro-inflammatory cytokines such as IL-8 or IL-18 and induces several anti-inflammatory mediators such as IL-1 receptor antagonist (IL-1Ra), soluble TNF receptor p55, IL-10 and IL-18 binding protein. However, the mechanisms of actions of IFN-α, and in particular individual IFN-α subtypes, are still only partly understood.

In patients with allergy or allergic disease, a Th2-predominant immune response is generated. Th2 cells secrete IL-4 and IL-13 driving B cells to produce Immunoglobulin E (IgE) antibodies specific to an allergen. An allergen is an antigen capable of stimulating a type-I hypersensitivity reaction in atopic individuals mainly through Immunoglobulin E (IgE)-mediated responses. Following that, IgE binds to its high affinity receptor on mast cells, skin cells and mucosal tissues. Upon exposure to the allergen, mast cells release their contents, which include histamine, leukotrienes and prostaglandins. This causes allergic symptoms including, but not limited to, red eyes, itchiness, runny nose, eczema, urticaria, angioedema, shortness of breath, wheezing, coughing an asthma attack, abdominal pain, vomiting diarrhoea or even anaphylaxis.

Allergic diseases are among the most common form of chronic illness. The World Health Organisation estimates that over 20 percent of the world population is affected and Europe alone has over 80 million sufferers (Global Allergy and Asthma European Network, 2008). An allergic reaction is usually caused by hypersensitivity of the immune system to an allergen, causing a misdirected immune response. Mild allergies, such as hay fever, are very common in the human population. Severe allergies can be caused by dietary allergens, such as food, by environmental allergens, such as the venom of stinging insects, by medication or can be genetically determined.

Food allergy is a major health concern, which is estimated to affect around 6% of young children and 3-4% of adults in Western societies. Food allergy is hypothesised to result from a breakdown in oral tolerance to ingested antigens or allergens. Food allergies and associated allergic diseases include, but are not limited to, dairy (milk) allergy, including Heiner syndrome, egg allergy, soya allergy, fish (shellfish) allergy, peanut and tree nut allergy, sesame and other seed allergy, gluten (wheat) and grains allergy, fruit and vegetable allergy, caffeine allergy, oral allergy syndrome, alcohol allergy, pollen food allergy syndrome, eosinophilic gastroenteritis, IgE mediated gastrointestinal food allergy and C1 esterase deficiency.

Management and treatment of allergic disease is usually via three general approaches: (i) avoidance of the allergen; (ii) medications that target disease symptoms and (iii) conventional immunotherapy, known as desensitisation, which aims to enhance the Th1 response in established disease. However, these approaches are far from ideal. Avoidance of allergens is not always possible, medications that target disease symptoms, such as anti-histamines, provide only short-term relief and desensitisation involves the use of the actual allergen, which can result in potentially frequent harmful side-effects. The possibility of anaphylaxis is never completely eliminated in patients suffering from allergic diseases and this causes a great deal of stress to the patient and their families.

Interferon subtypes IFN-α10 and IFN-α14 and hybrids thereof are discussed in PCT Publication Number WO2014/037717 and PCT Application Number PCT/GB2015/050717. In particular IFN-α10-IFN-α14 hybrids are disclosed that contain sequences characteristic of the IFN-α10 and IFN-α14 subtype binding sites based on a consensus backbone sequence of all 12 alpha-interferons, for example comprising an allergen, can result in enhanced activation of the Th1 immune response and suppression of the Th2/Th17 immune response. In particular, the inventor has developed hybrids of IFN-α10 and IFN-α14 containing higher affinity binding sites derived from each of IFN-α10 and IFN-α14 for the interferon receptors IFNR1 and IFNR2. In particular, the inventor demonstrates that it is advantageous to provide IFN-α10-IFN-α14 hybrids with high affinity binding sites derived from IFN-α10 and IFN-α14 subtypes that are not based on a consensus sequence of all 12 IFN-α subtypes which provide SEQ ID NO:3. The hybrids of the present invention are not based on a consensus backbone sequence of all 12 interferon-alphas. Instead, they derive the sequence characteristics of IFN-α10 and IFN-α14 subtypes without the sequence characteristics of the other 10 interferon-alpha subtypes.

In particular, the inventor has discovered that IFN-α10-IFN-α14 hybrid sequence comprising or consisting of at least one mutation selected from amino acids at positions 94, 101, 102, 109 or 144, (numbering as used in FIG. 16), in particular 94, 109 or 144 or combinations thereof, preferably

```
                                                          (SEQ ID NO: 3)
CDLPQTHSLGNRRALILLGQMGRISPFSCLKDRHDFRIPQEEFDGNQFQKAQAISVLHEM

MQQTFNLFSTENSSAAWEQTLLEKFSIELFQQMNDLEACVIQEVGVEETPLMNEDSILAV

RKYFQRITLYLIERKYSPCAWEVVRAEIMRSLSFSTNLQKRLRRKD.
```

It would be advantageous to provide alternative hybrids and further compositions and methods that provide alternative immunotherapeutic approaches.

The present inventor submits that it would be desirable to develop an improved immunotherapeutic approach which involves safer use of an allergen, as lower doses may be employed, and provides longer-term protection against the allergic reaction. Since allergy results from over-reactivity of Th2/Th17 cells and a corresponding lack of activity of the Th1 response, a medication that is able to modify and balance a misdirected Th2/Th17 response would be beneficial in preventing the allergic reaction. Such a medication would further be suitable to treat diseases and conditions where an exaggerated Th17 response plays a role, such as inflammatory bowel diseases. Additionally, the inventor considers the ability to enhance of a Th1-mediated immune response and suppress a Th2/Th17-mediated immune response would be useful in the provision of compositions that mediate immune response in subjects with cancer.

SUMMARY OF THE INVENTION

The present invention relates to the action of cytokines that promote the induction of a cell-mediated immune response (such as that mediated by Th1 cells) and cytokines that suppress a humoral or allergic immune response (such as that mediated by Th2 and Th17 cells). The present invention relates to hybrids of specific interferon (IFN) subtypes, and in particular to hybrids of IFN-α10 and IFN-α14.

Following extensive experimentation, the present inventor has made the surprising discovery that the administration of a specific interferon alpha (IFN-α) subtype which is a hybrid of IFN-α10 and IFN-α14, preferably wherein the hybrid includes the primary interferon receptor binding sites of IFN-α10 and IFN-α14 as part of a composition to modulate the immune system, such as a vaccine, for example comprising an allergen, can result in enhanced activation of the Th1 immune response and suppression of the Th2/Th17 immune response. In particular, the inventor has developed hybrids of IFN-α10 and IFN-α14 containing higher affinity binding sites derived from each of IFN-α10 and IFN-α14 for the interferon receptors IFNR1 and IFNR2. In particular, the inventor demonstrates that it is advantageous to provide IFN-α10-IFN-α14 hybrids with high affinity binding sites derived from IFN-α10 and IFN-α14 subtypes that are not based on a consensus sequence of all 12 IFN-α subtypes which provide SEQ ID NO:3. The hybrids of the present invention are not based on a consensus backbone sequence of all 12 interferon-alphas. Instead, they derive the sequence characteristics of IFN-α10 and IFN-α14 subtypes without the sequence characteristics of the other 10 interferon-alpha subtypes.

In particular, the inventor has discovered that IFN-α10-IFN-α14 hybrid sequence comprising or consisting of at least one mutation selected from amino acids at positions 94, 101, 102, 109 or 144, (numbering as used in FIG. 16), in particular 94, 109 or 144 or combinations thereof, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101,102,109 or 144 or more preferably at least five mutations selected from amino acids at positions 94, 101, 102, 109 or 144 or in particular SEQ ID NO:1 result in higher affinity binding of the interferon receptors IFNR1 and IFNR2. In embodiments, the IFN-α10-IFN-α14 hybrid sequence can be SEQ ID NO:3 further comprising the mutation(s) discussed above. These hybrid sequences can be used in all aspects and embodiments of the invention.

The inventor has surprisingly discovered that administration of the novel IFN-α10-IFN-α14 hybrids result in a greater reduction of IL-17 compared to previous IFN-α10-IFN-α14 hybrids. The inventor has discovered that administration of the novel IFN-α10-IFN-α14 hybrids result in a 10%, preferably a 20%, preferably a 30%, preferably a 40% and more preferably a 50% greater reduction of IL-17 compared to previous IFN-α10-IFN-α14 hybrids.

This has led to the identification by the inventor of improved therapeutic compositions which have utility in the treatment and/or prophylaxis of allergy and allergic diseases and diseases and conditions where an exaggerated Th17 response plays a role and also to cancer. In particular, the inventor has identified that the administration of at least one food allergen which is capable of mediating a Th2/Th17 immune response with a hybrid of IFN-α10 and IFN-α14 preferably wherein the hybrid includes the primary interferon receptor binding sites of IFN-α10 and IFN-α14 can be used in the treatment of food allergy and associated allergic diseases.

Moreover, the inventor has identified that the administration of a tumour antigen, either a tumour associated or a tumour specific antigen, in combination with a specific interferon alpha (IFN-α) subtype which is a hybrid of IFN-α10 and IFN-α14, preferably wherein the hybrid includes the primary interferon receptor binding sites of IFN-α10 and IFN-α14 as part of a composition to modulate the immune system, such as a vaccine, can be used in the treatment of cancer. Suitably, the cancer may be hepatic cancer, lung cancer, in particular non-small cell lung cancer, ovarian cancer, breast cancer, skin cancer, melanoma or genitourinary cancer.

Suitably, the tumour associated antigen may be selected from a prostate tumour, a renal cell tumour and a bladder tumour.

Accordingly a first aspect of the present invention provides a method for the treatment and/or prophylaxis of a condition where an enhancement of a Th1-mediated immune response and suppression of a Th2/Th17-mediated immune response are desired, said method comprising the step of:

(i) administering to a subject in need thereof a therapeutically effective amount of at least one interferon alpha subtype which is a hybrid of IFN-α10 and IFN-α14 wherein the hybrid includes the primary interferon receptor binding sites of IFN-α10 and IFN-α14.

Whilst not wishing to be bound by theory, the inventor believes that proteins comprising the amino acid sequence of IFN-α10 have greater affinity to interferon receptor 2 (IFNR2) and proteins comprising the amino acid sequence of IFN-α14 have greater affinity to interferon receptor 1 (IFNR1). Thus, substitution of a protein comprising an IFN-α10 amino acid sequence with amino acids of IFN-α14 which allow binding to interferon receptor 1 or substitution of a protein comprising an IFN-α14 amino acid sequence with amino acids of IFN-α10 which allow binding to interferon receptor 2 is considered to provide a IFN-α10 IFN-α14 hybrid protein which should have stronger binding affinity to both interferon receptors 1 and 2 than IFN-α10 or IFN-α14 alone. By including the primary interferon receptor binding sites of IFN-α10 and IFN-α14 is meant that the hybrid comprises amino acids selected from IFN-α10 and substituted into an IFN-α14 amino acid sequence to improve the ability of an IFN-α14 subtype to bind to an interferon receptor 2 and/or that the hybrid comprises amino acids selected from IFN-α14 and substituted into an IFN-α10 amino acid sequence to improve the ability of an IFN-α10 subtype to bind to an interferon receptor 1.

Suitably, several amino acid substitutions of protein comprising an IFN-α10 amino acid sequence with amino acids of IFN-α14 determined to be involved in binding to interferon receptor 1 may enhance the binding of the protein to interferon receptor 1. Suitably, an amino acid substitution of protein comprising an IFN-α14 amino acid sequence with amino acids of IFN-α10 determined to be involved in binding to interferon receptor 2 may enhance the binding of the protein to interferon receptor 2.

In embodiments the IFN-α10-IFN-α14 hybrid can substantially have the amino-acid sequence of IFN-α10, but be modified in a region between amino residues 80 to 150, or suitably between amino acid residues 84 to 144, or suitably amino acid residues 92 to 115 or suitably between amino acid residues 90 to 110, (utilizing the numbering of the IFN-α10 sequence providing in FIG. 16) to provide the amino acids provided by the IFN-α14 sequence. It is considered the amino acid residues in these regions or parts of these regions provide for the binding of IFN-α14 to interferon receptor 1. In particular, the hybrid sequence may include at least one, at least two, at least three, at least 4, at least 5, at least 6, at least 7, at least 8, at least 9, at least 10 or at least 11 modifications of the IFN-α10 sequence to provide the corresponding residues of the IFN-α14 sequence (suitably substituted residues are noted in bold in FIG. 9) or a conserved mutation thereof. In embodiments, eleven modifications are provided as indicated by the amino acids noted in bold in FIG. 9. In embodiments, the IFN-α10-IFN-α14 hybrid sequence may include at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144. In alternative embodiments, IFN-α14 can be utilised as a backbone structure of the hybrid and the residues which differ between the IFN-α10 and IFN-α14 sequences at the N and C terminal regions of the sequences can be provided in the hybrid sequence as those present in the IFN-α10 sequence. Suitably at least 1, at least 2, at least 3, at least 4, at least 5, at least 6, at least 7, at least 8, at least 9, at least 10 or at least 11 substitutions of the IFN-α14 N-terminal sequence may be made to provide the hybrid sequence to provide residues from IFN-α10 at those amino acid positions wherein the amino acids are not shared/common between IFN-α10 and IFN-α14. Suitably, at least 1, at least 2, or 3 substitutions are provided at the IFN-α14 C terminal sequence to provide residues from IFN-α10 to the hybrid sequence at those amino acid positions which are not shared/common between IFN-α10 and IFN-α14. In embodiments at least 1, at least 2, at least 3, at least 4, at least 5, at least 6, at least 7, at least 8, at least 9, at least 10 or at least 11 substitutions from the N-terminal sequence and at least 1, at least 2, or 3 substitutions from the C-terminal sequence of the IFN-α14 are made to provide residues from IFN-α10 to the hybrid at those amino acid positions which have amino acids that are not shared/common between IFN-α10 and IFN-α14.

In embodiments, the hybrid comprises or consists of an amino acid sequence SEQ ID NO: 1 or a functionally active fragment or variant thereof.

In certain embodiments, the method includes a step of administering to the subject a therapeutically effective amount of a vaccine composition for treatment or prophylaxis of the condition where an enhancement of a Th1-mediated immune response and suppression of a Th2/Th17-mediated immune response are desired. The vaccine composition may be administered sequentially, separately or simultaneously with the at least one interferon alpha subtype.

By functionally active is meant an IL-α10 IL-α14 hybrid peptide comprising the primary interferon binding sites of IFN-α10 and IFN-α14 wherein the administration of peptide to a subject or expression of peptide in a subject promotes enhancement of Th1 mediated immune response and suppression of a Th2/Th17 mediated immune response. Further, functional activity may be indicated by the ability of a hybrid peptide to enhance a Th1 mediated immune response and to suppress a Th2/Th17 mediated response.

A fragment can comprise at least 50, preferably 100 and more preferably 150 or greater contiguous amino acids from SEQ ID NO: 1 and which is functionally active. Suitably, a fragment may be determined using, for example, C-terminal serial deletion of cDNA such as SEQ ID NO: 2. Said deletion constructs may then be cloned into suitable plasmids. The activity of these deletion mutants may then be tested for biological activity as described herein.

By variant is meant an amino acid sequence which is at least 70% homologous to SEQ ID NO: 1, more preferably at least 80% homologous to SEQ ID NO: 1, more preferably at least 90% homologous to SEQ ID NO: 1, even more preferably at least 95% homologous to SEQ ID NO: 1, even more preferably at least 96% homologous to SEQ ID NO: 1, even more preferably at least 97% homologous to SEQ ID NO: 1 and most preferably at least 98% homology with SEQ ID NO: 1. A variant encompasses a polypeptide sequence of SEQ ID NO: 1 which includes substitution of amino acids, especially a substitution(s) which is/are known for having a high probability of not leading to any significant modification of the biological activity or configuration, or folding, of the protein. These substitutions, typically known as conserved substitutions, are known in the art. For example the group of arginine, lysine and histidine are known interchangeable basic amino acids. Suitably, in embodiments amino acids of the same charge, size or hydrophobicity may be substituted with each other. Suitably, any substitution may be selected based on analysis of amino acid sequence alignments of interferon alpha subtypes to provide amino acid substitutions to amino acids which are present in other alpha subtypes at similar or identical positions when the sequences are aligned. Hybrids, and variants and fragments thereof may be generated using suitable molecular biology methods as known in the art.

In certain embodiments, the vaccine composition comprises at least one antigen. In certain embodiments, the vaccine composition comprises at least one allergen capable of mediating a Th2/Th17 immune response, for example, a food allergen.

In aspects and embodiments of the invention the antigen can be a tumour antigen, for example a tumour specific antigen or a tumour associated antigen, in particular a tumour antigen can be of a hepatic carcinoma, lung cancer, in particular non-small cell lung cancer, ovarian cancer, breast cancer, skin cancer, melanoma or of a genitourinary cancer. In particular an antigen of a genitourinary cancer can include an antigen from a prostate cancer, renal cell carcinoma, or bladder cancer. Suitably, an antigen may be a tumour specific antigen or tumour associated antigen provided in an existing cancer vaccine in use or development which would benefit from an adjuvant that enhances T-cell immunity, in particular that enhances a Th1 response or provides an enhancement of a Th1 mediated immune response and suppression of a Th2/Th17-mediated immune response. Suitably a tumour specific or tumour-associated antigen may be obtained from a tumour of a subject to be treated. In embodiments only a tumour-associated antigen can be used.

In embodiments a tumour antigen, in particular an associated antigen may be an antigen for a prostate cancer antigen, in particular prostate-specific antigen. Suitably a method of providing a prostate specific antigen or a prostate cancer antigen with the interferon-alpha subtypes of the invention maybe used to treat prostate cancer, specifically castration-resistant prostate cancer.

As will be appreciated by a physician, the subjects who will benefit most from such treatments may be those with minimal disease, as there may be less chance of increasing tumour suppression of the immune system, additionally or alternatively such treatments may benefit subjects with advanced disease who may have significant tumour immune suppression and may benefit more from the use of vaccines in combination with other forms of treatment. Suitably the use of vaccines including tumour antigens, in particular tumour associated antigen may be in combination with other forms of immunotherapy, for example Sunitinib (Sutent by Pfizer) a tyrosine kinase inhibitor.

In embodiments specific tumour antigens, in particular tumour-associated antigens may be selected from the antigens utilised in the prostate cancer vaccines TroVax and Prostvac.

In embodiments a tumour antigen, in particular a tumour-associated antigen can be selected from renal cell carcinoma. Suitably a tumour antigen, for example a tumour-associated antigen for renal cell carcinoma may be selected from a heat shock protein or proteins of renal tumour cell lysates, in particular the antigen used in the potential vaccine MVA-5T4.

Suitably a tumour antigen may be MUC1 from melanoma.

In embodiments, a tumour antigen, for example a tumour-associated antigen can be selected from bladder cancer. Suitably a tumour-associated antigen may be selected from Bacille Calmette-Guerin (BCG) vaccine, human leukocyte antigen—A*2402 restricted epitope peptides, immucin peptide (a 21mer synthetic vaccine composed of the entire signal peptide of the MUC1 protein) human chorionic gonadotropin-colony stimulating factor, or human chorionic gonadotropin-beta.

In certain embodiments, the method therefore includes a step of administering to the subject a therapeutically effective amount of at least one allergen capable of mediating a Th2/Th17 immune response, for example, a food allergen or tumour antigen, for example a tumour associated antigen. The allergen maybe administered sequentially, separately or simultaneously with the at least one interferon alpha subtype.

Typically, the subject is a mammal, in particular a human. In certain embodiments, the subject can be suffering from a condition where an enhancement of a Th1-mediated immune response and suppression of a Th2/Th17-mediated immune response are desired.

According to a second aspect of the present invention, there is provided at least one interferon alpha subtype which is a hybrid of IFN-α10 and IFN-α14 wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, in particular SEQ ID NO:1 or a fragment or variant thereof for use in the treatment and/or prophylaxis of a condition where an enhancement of a Th1-mediated immune response and suppression of a Th2/Th17-mediated immune response are desired.

In certain embodiments, the at least one interferon alpha subtype, in particular a hybrid IFN-α10 and IFN-α14 subtype, for example SEQ ID NO: 1, as described herein is provided for simultaneous, separate or sequential administration with a vaccine composition for treatment or prophylaxis of the condition where an enhancement of a Th1-mediated immune response and suppression of a Th2/Th17-mediated immune response are desired. In certain embodiments, the at least one interferon alpha subtype is provided for simultaneous, separate or sequential administration with at least one allergen capable of mediating a Th2/Th17 immune response there against, for example, a food allergen, or a tumour antigen, in particular a tumour-associated antigen.

According to a third aspect of the present invention, there is provided use of at least one interferon alpha subtype which is a hybrid of IFN-α10 and IFN-α14 wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, in particular wherein the hybrid can be SEQ ID No:1 or a variant or fragment thereof in the preparation of a medicament for the treatment and/or prophylaxis of a condition where an enhancement of a Th1-mediated immune response and suppression of a Th2/Th17-mediated immune response are desired.

In certain embodiments, the at least one interferon alpha subtype is provided for simultaneous, separate or sequential administration with a vaccine composition for treatment or prophylaxis of the condition where an enhancement of a Th1-mediated immune response and suppression of a Th2/Th17-mediated immune response are desired. In certain embodiments, the at least one interferon alpha subtype is provided for simultaneous, separate or sequential administration with at least one allergen capable of mediating a Th2/Th17 immune response there against, for example, a food allergen, or a tumour antigen, in particular a tumour associated antigen.

According to a further aspect of the present invention, there is provided a composition comprising:
(i) a vaccine for treatment or prophylaxis of a condition where an enhancement of a Th1-mediated immune response and suppression of a Th2/Th17-mediated immune response are desired; and
(ii) at least one interferon alpha subtype which is a hybrid of IFN-α10 and IFN-α14, in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101,102,109 or 144, preferably at least two mutations selected from amino acids at positions 94, 101, 102, 109 or 144, more preferably at least three mutations selected from amino acids at positions 94, 101, 102,109 or 144, more preferably at least four mutations selected from amino acids at positions 94, 101, 102, 109 or 144 or more preferably at least five mutations selected from amino acids at positions 94, 101, 102, 109 or 144, in particular wherein the hybrid can be SEQ ID NO:1 or a variant or fragment, as described herein.

In certain embodiments, the vaccine comprises at least one allergen capable of mediating a Th2/Th17 immune response, for example, a food allergen or a tumour antigen, in particular a tumour-associated antigen.

A further aspect of the present invention provides a pharmaceutical composition for enhancement of a Th1 mediated immune response and suppression of a Th2/Th17-mediated immune response, wherein the composition comprises a vaccine for treatment or prophylaxis of a condition where an enhancement of a Th1-mediated immune response and suppression of a Th2/Th17-mediated immune response are desired and at least one interferon alpha subtype which is a hybrid of IFN-α10 and IFN-α14, in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least Five mutations selected from amino acids at positions 94, 101, 102, 109 or 144, in particular wherein the hybrid can be SEQ ID NO:1 or a fragment or variant thereof along with a pharmaceutically acceptable excipient, diluent or carrier.

In certain embodiments, the vaccine comprises at least one allergen capable of mediating a Th2/Th17 immune response, for example, a food allergen or tumour antigen, in particular a tumour-associated antigen.

In a further aspect, the present invention extends to improvements in the efficacy of vaccines, for example, anti-allergy or allergic disease vaccines or tumour or cancer vaccines, in particular genitourinary cancer vaccines, for example prostate cancer, renal cancer and or bladder cancer. A composition which comprises a vaccine for treatment or prophylaxis of a condition where an enhancement of a Th1-mediated immune response and suppression of a Th2/Th17-mediated immune response are desired, such as at least one allergen capable of mediating a Th2/Th17 immune response, and at least one interferon alpha subtype which is a hybrid of IFN-α10 and IFN-α14 in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, in particular SEQ ID NO:1 or a variant or fragment thereof, has been surprisingly identified by the inventor as providing an unexpectedly efficacious composition for the treatment and/or prophylaxis of diseases, such as allergy or associated allergic diseases.

Accordingly, a further aspect of the present invention provides a vaccine composition comprising;
(i) a vaccine for treatment or prophylaxis of a condition where an enhancement of a Th1-mediated immune response and suppression of a Th2/Th17-mediated immune response are desired; and
(ii) at least one interferon alpha subtype which is a hybrid of IFN-α10 and IFN-α14 in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, in particular can be SEQ ID NO:1 or a variant or fragment thereof.

In certain embodiments, the vaccine comprises at least one allergen capable of mediating a Th2/Th17 immune response, for example, a food allergen or a tumour antigen, in particular a tumour-associated antigen.

A further aspect of the present invention provides a vaccine composition for use in the treatment and/or prophylaxis of allergy or cancer, in particular genitourinary cancer, for example prostate cancer, renal cancer or bladder cancer, where an enhancement of a Th1-mediated immune response and the suppression of a Th2/Th17-mediated immune response are desired, said vaccine composition comprising;
(i) at least one allergen capable of mediating a Th2/Th17 immune response; and
(ii) at least one interferon alpha subtype which is a hybrid IFN-α10 and IFN-α14 subtype, in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102,109 or 144, more preferably at least four mutations selected from amino acids at positions 94, 101, 102, 109 or 144 or more preferably at least five mutations selected from amino acids at positions 94, 101, 102, 109 or 144, in particular wherein the hybrid can be SEQ ID NO:1 or a variant or fragment, as described herein.

A further aspect of the present invention provides for the use of a vaccine composition comprising at least one allergen capable of mediating a Th2/Th17 immune response and at least one interferon alpha subtype which is a hybrid of IFN-α10 and IFN-α14 in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102,109 or 144, in particular wherein the hybrid can be SEQ ID NO:1 or a variant or fragment thereof, in the preparation of a medicament for the treatment and/or prophylaxis of allergy or associated allergic diseases, or cancer, in particular genitourinary cancer, for example prostate cancer, renal cancer or bladder cancer.

A further aspect of the present invention provides a method for the treatment and/or prophylaxis of allergy or associated allergic diseases or of cancer, in particular genitourinary cancer for example prostate cancer, renal cancer or bladder cancer the method comprising the step of:
(i) administering a therapeutically effective amount of a vaccine composition or an immunogenic composition which comprises at least one allergen capable of mediating a Th2/Th17 immune response and at least one interferon alpha subtype which is a hybrid of IFN-α10 and IFN-α14, in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, in particular wherein the hybrid can be SEQ ID NO:1 or a fragment or variant thereof to a subject in need thereof.

According to a further aspect of the present invention, there is provided a method for the treatment and/or prophylaxis of a condition mediated by enhanced expression of IL-17, said method comprising the step of:
(i) administering to a subject in need thereof a therapeutically effective amount of at least one interferon alpha subtype which is a hybrid of IFN-α10 and IFN-α14 in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, in particular SEQ ID NO:1 or a fragment or variant thereof.

According to a further aspect of the present invention, there is provided at least one interferon alpha subtype comprising or consisting of an IFN-α10 and IFN-α14 hybrid in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, in particular SEQ ID NO:1 or a variant or fragment thereof for use in the treatment and/or prophylaxis of a condition mediated by enhanced expression of IL-17.

Suitably, in aspects and embodiments of the invention, the hybrid may comprise or consist of the amino acid sequence of SEQ ID NO:1.

According to a further aspect of the present invention, there is provided use of at least one interferon alpha subtype IFN-α10 and IFN-α14 hybrid in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, in particular SEQ ID NO:1 or a variant or fragment thereof, in the preparation of a medicament for the treatment and/or prophylaxis of a condition mediated by enhanced expression of IL-17.

According to a further aspect of the present invention, there is provided a method for modulating an immune response, said method comprising the step of:
(i) administering to a subject in need thereof a therapeutically effective amount of at least one interferon alpha subtype IFN-α10 and IFN-α14 hybrid, wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, and in particular can be SEQ ID NO:1 or a variant or fragment thereof.

Suitably, in aspects and embodiments of the invention, the administration or use of at least one interferon alpha subtype comprising or consisting of an IFN-α10 and IFN-α14 hybrid in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, in particular SEQ ID NO:1 or a variant or fragment thereof results in the full or partial inhibition of IL-17 and/or the full or partial activation of IFN-γ.

According to a further aspect of the present invention, there is provided at least one interferon alpha subtype IFN-α10 and IFN-α14 hybrid, wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, and in particular can be SEQ ID NO:1 or a variant or fragment thereof for use in modulating an immune response.

According to a further aspect of the present invention, there is provided use of at least one interferon alpha subtype hybrid IFN-α10 and IFN-α14 subtype, wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, and in particular SEQ ID NO:1 or a variant or fragment thereof in the preparation of a medicament for modulating an immune response.

In certain embodiments of the aspects of the invention outlined above, the at least one interferon alpha subtype is provided for simultaneous, separate or sequential administration with a vaccine for treatment or prophylaxis of the condition where an enhancement of a Th1-mediated immune response and suppression of a Th2/Th17-mediated immune response are desired, for example, a vaccine for the treatment or prophylaxis of a condition mediated by enhanced expression of IL-17, e.g. an inflammatory disease or condition or an autoimmune disease, such as inflammatory bowel disease (IBD), ulcerative colitis (UC) or Crohn's disease (CD), cancer, suitably hepatic cancer, lung cancer, in particular non-small cell lung cancer, ovarian cancer, breast cancer, skin cancer, melanoma or genitourinary cancer, in particular genitourinary cancer, for example prostate cancer, renal cancer or bladder cancer. In certain embodiments, the vaccine composition comprises at least one antigen. In certain embodiments, the vaccine comprises at least one allergen capable of mediating a Th2/Th17 immune response there against, for example, a food allergen.

In certain embodiments the antigen can be a tumour antigen in particular a tumour specific and/or a tumour-associated antigen.

In certain embodiments of the aspects of the invention outlined above, the at least one IFN-α subtype comprises, consists of or is an IFN-α10 IFN-α14 hybrid such as a fusion protein, or recombinant protein or the like which includes the primary interferon receptor binding sites of IFN-α10 and IFN-α14, and in particular which comprises or consists of the amino acid sequence SEQ ID NO:1 or a variant or fragment thereof. In embodiments the IFN-α10 IFN-α14 hybrid can be glycosylated. Suitably the IFN-α10 IFN-α14 hybrid can be glycosylated in a similar fashion to IFN-α14.

In certain embodiments of the aspects of the invention outlined above, the at least one allergen is at least one food allergen or a tumour specific or tumour-associated tumour allergen, for example a prostate cancer allergen, a renal cancer allergen and or bladder cancer allergen. In certain embodiments, the at least one allergen is a dietary allergen such as food, an environmental allergen such as the venom of stinging insects, or a medication.

In a further aspect of the invention there is provided a recombinant polypeptide comprising or consisting of SEQ ID NO:1 or a fragment or variant thereof. Nucleic acid sequences derived from the amino acid sequence SEQ ID NO:1 are provided as SEQ ID NO:2. These nucleic acid sequences can form additional aspects to the invention.

In certain embodiments of the aspects of the invention outlined above, the at least one food allergen is selected from the group consisting of, but not limited to, corn, garlic, oats, coffee, chocolate, pickle, wheat or gluten and their products or derivatives which include durum wheat, spelt (*triticum spelta*), kamut (*triticum poloncium*), couscous, bran, wheat bran, wheat germ, wheat gluten, farina, rusk, semolina, durum wheat semolina, flour, wholewheat flour, wheat flour, wheat starch, starch, modified starch, hydrolysed starch, food starch, edible starch, vegetable starch, vegetable gum, vegetable protein, cereal filler, cereal binder, cereal protein;

tree nuts (including almonds, cashews, macademia, walnut and brazil nuts); seeds, including sesame, sunflower and poppy seeds; dairy derived antigens, such as milk or milk derivatives, including cheese and yoghurt; fish or shellfish or their derivatives, including from the mollusc phylum (gastropod class: snails and abalone; bivalve class: clam, mussel and oyster; cephalopod class: octopus, squid and scallop), arthropod phylum (crustacean family: crab, lobster, shrimp, prawn and crayfish) or chordate phylum (cartilaginous family: ray and shark; bony fish: cod, salmon and tuna); eggs or egg derivatives; monosodium glutamate (MSG); sulphites or sulphur dioxide; legume allergies to the leguminosae family, which includes peanut, soya (soybean or soya derivatives), bean seeds, peas, green beans, lentils, carob and liquorice; other vegetable allergies such as potato; fruit allergies to the rosaceae family, which includes apple, pear, cherry, peach and plum; fruit allergies to the cucurbitaceae family, which includes cucumber, melon, watermelon, zucchini and pumpkin; and other fruit allergies such as those developed against kiwi, banana, avocado, tomatoes, strawberries and raspberries.

In certain embodiments, the vaccine or vaccine composition can be a vaccine composition for the treatment or prophylaxis of a condition mediated by enhanced expression of IL-17, e.g. an inflammatory disease or condition or an autoimmune disease, such as inflammatory bowel disease (IBD), ulcerative colitis (UC) or Crohn's disease (CD), or cancer, suitably hepatic cancer, lung cancer, non-small cell lung cancer, ovarian cancer, breast cancer, skin cancer, melanoma or genitourinary cancer, in particular genitourinary cancer, for example prostate cancer, renal cancer or bladder cancer. In certain embodiments, the vaccine or vaccine composition can be a vaccine composition for the treatment or prophylaxis of an inflammatory disease or condition or an autoimmune disease, such as inflammatory bowel disease (IBD), ulcerative colitis (UC) or Crohn's disease (CD).

In certain embodiments of the aspects of the invention outlined above, the condition where an enhancement of a Th1-mediated immune response and the suppression of a Th2/Th17-mediated immune response are desired can be a condition mediated by enhanced expression of IL-17, e.g. an inflammatory disease or condition or an autoimmune disease, such as inflammatory bowel disease (IBD), ulcerative colitis (UC) or Crohn's disease (CD).

In certain embodiments of the aspects of the invention outlined above, the condition where an enhancement of a Th1-mediated immune response and the suppression of a Th2/Th17-mediated immune response are desired can be an inflammatory disease, in particular an inflammatory disease which is mediated by an exaggerated or overactive Th17 immune response. In certain embodiments of the aspects of the invention outlined above, the condition where an enhancement of a Th1-mediated immune response and the suppression of a Th2/Th17-mediated immune response are desired can be an autoimmune disease, in particular an autoimmune disease which is mediated by an exaggerated or overactive Th17 immune response. For example, in certain embodiments the condition can be inflammatory bowel disease (IBD), such as ulcerative colitis (UC) or Crohn's disease (CD). In certain embodiments, the condition can be selected from the group consisting of asthma, allergic rhinitis, atopic dermatitis and food allergy. In certain embodiments, the condition is cancer, in particular a genitourinary cancer, in particular prostate cancer, bladder cancer or renal cancer.

In certain embodiments of the aspects of the invention outlined above, the condition where an enhancement of a Th1-mediated immune response and the suppression of a Th2/Th17-mediated immune response are desired is an allergy or associated allergic diseases and conditions caused thereby, or cancer wherein an immune response is desired against a tumour-associated antigen, in particular a tumour associated antigen of prostate cancer, renal cancer or bladder caner. In particular, in certain embodiments the condition is a food allergy including food associated or derived allergies and associated allergic diseases and conditions caused thereby.

In certain embodiments, the food allergy associated allergic diseases or conditions include, but are not limited to, milk/dairy allergy, including Heiner syndrome, egg allergy, soya allergy, fish (shellfish) allergy, peanut and tree nut allergy, sesame and other seed allergy, wheat and grains allergy, fruit and vegetable allergy, caffeine allergy, oral allergy syndrome, alcohol allergy, pollen food allergy syndrome, eosinophilic gastroenteritis, IgE mediated gastrointestinal food allergy and C1 esterase deficiency.

In certain embodiments of the present invention, the method of administration is oral administration. In certain embodiments, the method of administration is sublingual or buccal administration. In certain embodiments, the method of administration involves placing a lozenge under the patient's tongue. In certain embodiments, the route of administration is ocular or by means of introduction into the nasal cavity, by way of nasal administration. Also it may be introduced by oral administration (swallowing) of a capsule or similar device into the small intestine/duodenum such that the capsule does not dissolve in the stomach, but bypasses same and delivers/releases the interferon alpha subtype only into the small intestine/duodenum.

DETAILED DESCRIPTION OF THE INVENTION

The inventor of the present invention has surprisingly discovered that administering an IFN-α subtype which is a hybrid of IFN-α10 and IFN-α14 subtypes, for example SEQ ID NO:1, as described herein results in the enhancement of a Th1 T cell mediated immune response and the suppression of a Th2/Th17 T cell mediated immune response and can therefore skew the immune response towards a cell-mediated (Th1) path, whilst simultaneously suppressing the allergic (Th2/Th17) response. Surprisingly, this effect is enhanced when the IFN-α subtype is administered orally.

In particular, the inventor discovered that IFN-α10-IFN-α14 hybrids that contain sequences characteristic of the IFN-α10 and IFN-α14 subtype binding sites that are not based on a consensus sequence of all 12 IFN-α subtypes resulted in a protein with higher affinity binding sites for the two interferon receptors, IFNR1 and IFNR2. This finding can be applied to provide an improved method and improved adjuvant composition for treating and/or preventing conditions where the enhancement of a Th1 T cell mediated immune response and/or the suppression of a Th2/Th17 T cell mediated immune response are desired, for example, inflammatory, autoimmune or allergy conditions, or cancer (including malignant conditions), in particular genitourinary cancers, in particular prostate cancer, renal cancer or bladder cancer. In particular, the hybrid of IFN-α10 and IFN-α14, in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, and in particular SEQ ID NO:1 or a fragment or variant thereof may be used as an adjuvant in vaccines to boost immune response to antigens and direct the immune response towards a Th1 immune response.

The inventor has also discovered that a combination of a vaccine composition or a food or tumour specific or tumour-associated antigen allergen which is capable of mediating a Th2/Th17 immune response and an IFN-α subtype which is a hybrid of IFN-α10 and IFN-α14, in particular a hybrid comprising the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, and in particular SEQ ID NO:1 or a fragment or variant thereof can result in the activation of a Th1 T cell mediated immune response and the suppression of a Th2/Th17 T cell mediated immune response.

Tumour progression in normal immunocompetent subjects may reflect a failure of the immune system to recognize the tumour antigens or a subversion of the anti-tumour immune response through induction and activation of regulatory T cells. In subjects with hepatic choriocarcinoma (HCC) studies of IL-17 α cells have suggested a potential pro-tumour role for IL-17. Increased IL-17 producing cell density within the tumours of HCC patients correlates with both microvessel density and poor prognosis. Further, in subjects with non-small cell lung and ovarian cancer, higher levels of IL-17 within the tumour correlated with higher blood vessel density and shorter survival. Additionally IL-17 has been suggested to have pro-angiogenic roles and this has not been restricted to particular cell populations. Moreover, it has been shown that IL-17A or IL-17A producing cells are elevated in the environment of breast tumours and correlate with poor prognosis.

Isolation of tumour infiltrating lymphocytes (TILS) from breast cancer biopsies revealed these cells secreted significant amounts of IL-17A, and that recombinant IL-17A recruits the MAPK pathway by upregulating phosphorylated ERK ½ in human breast cancer lines thereby promoting proliferation and resistance to conventional chemotherapeutic agents such as Docetaxel. IL-17A has also been indicated to stimulate migration and invasion of breast cancer cells. Importantly IL-17A-neutralizing antibodies abrogated these effects, demonstrating the pathophysiological role of IL-17A as a potential therapeutic target for breast cancer. The inventor has surprisingly discovered that administration of the novel IFN-α10-IFN-α14 hybrid result in a greater reduction of IL-17 compared to previous IFN-α10-IFN-α14 hybrid. The inventor has discovered that administration of the novel IFN-α10-IFN-α14 hybrid results in a 10%, preferably a 20%, preferably a 30%, preferably a 40% and more preferably a 50% greater reduction of IL-17 compared to previous IFN-α10-IFN-α14 hybrid. The determination by the inventor or means thus to activate a Th1 T cell mediated immune response and suppress a Th2/Th17 T cell mediated immune response is therefore significant and of utility in cancer. Thus, the present invention may be used for the treatment and prophylaxis of any known cancerous or malignant condition.

In addition, the inventor has discovered that the administration or use of at least one interferon alpha subtype comprising or consisting of an IFN-α10 and IFN-α14 hybrid in particular wherein the hybrid comprises the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, in particular SEQ ID NO:1 or a variant or fragment thereof results in the full or partial inhibition of IL-17 and/or the full or partial activation of IFN-γ.

Moreover, the inventor has surprisingly discovered that orally administering the antigen and IFN-α subtype which is a hybrid of IFN-α10 and IFN-α14 in particular a hybrid comprising the primary interferon binding sites of IFN-α10 and IFN-α14, in particular wherein the IFN-α10-IFN-α14 hybrid sequence comprises at least one mutation selected from amino acids at positions 94, 101, 102, 109 or 144, preferably at least two mutations selected from amino acids at positions 94, 101, 102, 109 or 144, more preferably at least three mutations selected from amino acids at positions 94, 101, 102, 109 or 144, more preferably at least four mutations selected from amino acids at positions 94, 101, 102, 109 or 144 or more preferably at least five mutations selected from amino acids at positions 94, 101, 102, 109 or 144, and in particular SEQ ID NO:1 or a fragment or variant thereof in combination as discussed herein can result in the activation of a Th1 T cell mediated immune response and the suppression of a Th2/Th17 T cell mediated immune response. A standard flu vaccine was mixed with a low dose of leukocyte-derived interferon alpha (LDA1) and orally administered to mice. The inventor noted that without the interferon, a small anti-flu antibody response was recorded in mice, which was approximately 50 times less than with an injected vaccine. With interferon-alpha, the response from the orally delivered vaccine was exactly the same as the injected vaccine. A series of buccal immunisations using a standard protein antigen and two interferons, LDA1 and an isolated subtype IFN-α14, surprisingly resulted in oral immunisation of mice to which the composition was administered. However, the inventor surprisingly noted that while the LDA1 gave a balanced response, IFN-α14 mediated only a significant humoral response. The production of IgG1 is indicative of a Th2 response (humoral immunity) and the production of IgG2*a* is indicative of a Th1 response (cell-mediated immunity).

The inventor, whilst not wishing to be bound by theory, has identified that the oral administration of a food allergen capable of mediating a Th2/Th17 immune response and an interferon alpha subtype which is a hybrid of IFN-α10 and IFN-α14 can skew the immune response towards a cell-mediated (Th1) path, whilst simultaneously suppressing the allergic (Th2/Th17) response. Accordingly, the inventor has surprisingly shown that the co-administration of an allergen such as a food derived antigen that is causative of allergy or associated allergic diseases in a subject with certain interferon subtypes modulates the resulting immune response and skews it away from the Th2/Th17 response which would have been expected to develop against the allergen or antigen. This surprising finding provides an unexpected approach to treat or prevent allergic responses or diseases which occur in subjects as a result of allergens such as food-derived allergens or tumour associated antigens.

DEFINITIONS

Subject

As herein defined, a "subject" includes and encompasses mammals such as humans, primates and livestock animals (e.g. sheep, pigs, cattle, horses, donkeys); laboratory test animals such as mice, rabbits, rats and guinea pigs; and companion animals such as dogs and cats.

Treatment/Therapy

The term "treatment" is used herein to refer to any regimen that can benefit a human or non-human animal. The treatment may be in respect of any existing inflammatory, autoimmune, allergic or allergy-associated condition and the treatment may be prophylactic (preventative treatment). Treatment may include curative or alleviative effects. Reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition. Accordingly, therapeutic and/or prophylactic treatment includes amelioration of the symptoms of a particular allergic condition or preventing or otherwise reducing the risk of developing a particular allergic condition. The term "prophylactic" may be considered as reducing the severity or the onset of a particular condition. "Therapeutic" may also reduce the severity of an existing condition.

Administration

The active ingredients used in the present invention (e.g. vaccine or allergen and IFN-α10, IFN-α14 or a hybrid thereof) in particular a hybrid IFN-α10 and IFN-α14 subtype, for example SEQ ID NO: 1, as described herein can be administered separately to the same subject, optionally sequentially, or can be co-administered simultaneously as a pharmaceutical, immunogenic or vaccine composition. In certain embodiments, the vaccine or allergen is co-administered with the interferon alpha subtype. The pharmaceutical composition will generally comprise a suitable pharmaceutical excipient, diluent or carrier selected depending on the intended route of administration.

The active ingredients can be administered to a patient in need of treatment via any suitable route. The precise dose will depend upon a number of factors, as is discussed below in more detail.

One suitable route of administration is parenterally (including subcutaneous, intramuscular, intravenous, by means of, for example a drip patch). Other suitable routes of administration include (but, are not limited to) oral, ocular, nasal, topical (including buccal and sublingual), infusion, intradermal or administration via oral or nasal inhalation, by means of, for example, a nebuliser or inhaler, or by an implant. Preferable routes of administration include (but, are not limited to) oral, buccal and sublingual. The compositions of the invention may also be administered in such a manner that they are directed to, or released in, specific areas of the gut intestinal tract (such as the small intestine/duodenum). Typically such release will occur after passage through the stomach, this targeted release being achievable through the use of coatings and the like.

For intravenous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, Lactated Ringer's injection. Preservatives, stabilisers, buffers, antioxidants and/or other additives may be included, as required.

The compositions of the present invention for oral administration may be in tablet, capsule, lozenge, powder or liquid form. Oral administration may involve placing a lozenge under the tongue of the patient A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The compositions of the present invention may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Examples of the techniques and protocols mentioned above and other techniques and protocols which may be used in accordance with the invention can be found in Remington's Pharmaceutical Sciences, 18th edition, Gennaro, A.R., Lippincott Williams & Wilkins; 20th edition (Dec. 15, 2000) ISBN 0-912734-04-3 and Pharmaceutical Dosage Forms and Drug Delivery Systems; Ansel, H.C. et al. 7$^{th}$ Edition ISBN 0-683305-72-7, the entire disclosures of which are herein incorporated by reference.

Pharmaceutical Compositions

As described above, the present invention extends to a pharmaceutical composition for the treatment of inflammatory diseases, autoimmune diseases and allergy such as food allergy and associated allergic diseases and, in particular, for the induction of a Th1 immune response and the suppression or inhibition of a Th2/Th17 immune response.

Pharmaceutical compositions according to the present invention, and for use in accordance with the present invention, may comprise, in addition to an active ingredient, a pharmaceutically acceptable excipient, carrier, buffer stabiliser or other materials well known to those skilled in the art. Such materials should be non-toxic and should not interfere with the efficacy of the active ingredient. The precise nature of the carrier or other material will depend on the route of administration, which may be, for example, oral, intravenous, intranasal or via oral or nasal inhalation. The formulation may be a liquid, for example, a physiologic salt solution containing non-phosphate buffer at pH 6.8-7.6, or a lyophilised or freeze-dried powder.

Dose

The composition is preferably administered to an individual in a "therapeutically effective amount" or a "desired amount", this being sufficient to show benefit to the individual. As defined herein, the term an "effective amount" means an amount necessary to at least partly obtain the desired response, or to delay the onset or inhibit progression or halt altogether the onset or progression of a particular condition being treated. The amount varies depending upon the health and physical condition of the subject being treated, the taxonomic group of the subject being treated, the degree of protection desired, the formulation of the composition, the assessment of the medical situation and other relevant factors. It is expected that the amount will fall in a relatively broad range, which may be determined through routine trials. Prescription of treatment, e.g. decisions on dosage etc., is ultimately within the responsibility and at the discretion of general practitioners, physicians or other medical doctors, and typically takes account of the disorder to be treated, the condition of the individual patient, the site of delivery, the method of administration and other factors known to practitioners. The optimal dose can be determined by physicians based on a number of parameters including, for example, age, sex, weight, severity of the condition being treated, the active ingredient being administered and the route of administration. A broad range of doses may be applicable. Considering oral administration to a human patient, for example, from about 10 µg to about 1000 µg of agent may be administered per human dose, optionally for 3 to 4 doses. Dosage regimes may be adjusted to provide the optimum therapeutic response and reduce side effects. For example, several divided doses may be administered daily, weekly, monthly or other suitable time intervals or the dose may be proportionally reduced as indicated by the exigencies of the situation.

Unless otherwise defined, all technical and scientific terms used herein have the meaning commonly understood by a person who is skilled in the art in the field of the present invention.

Autoimmune Disease

The term "autoimmune disease" as used herein is understood to mean any disease or condition which is caused by a body's tissues being attacked by its own immune system.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

The present invention will now be exemplified with reference to the following non-limiting Figures and examples which are provided for the purpose of illustration and are not intended to be construed as being limiting on the present invention. Other embodiments of this invention will be apparent to those of ordinary skill in the art in view of this description.

BRIEF DESCRIPTION OF THE FIGURES

FIG. 9 shows the IFN-α10 and IFN-α14 hybrid amino acid sequence which contains the 2 interferon receptor (IFNaR1 and IFNaR2) binding sites.

Based on the protein sequence SEQ ID NO:1 using online webservices (for example, EMBOSS Backtranseq), a nucleic acid sequence can be obtained. FIG. 10 provides the reverse translation of the protein sequence SEQ ID NO:1 when an *E. coli* codon usage table is used.

EXAMPLE 1

Identification of Interferon-Alpha Subtypes that are Immunological Adjuvants

50 µg ovalbumin and $10^5$ IU of interferon subtypes IFN-α14, IFN-α2, IFN-α21, IFN-α10, an IFN "mix" (including IFN-α1, IFN-α8, IFN-α21 and possibly IFN-α17), IFN-α8, Intron A, MULTIFERON™ and IFN-α1 in 50 µl were administered via intraperitoneal injection three times per week to BALB-c female mice, in groups of 10.

The serum concentrations of IgG1 mg/ml (Th2 response—humoral immunity to the ovalbumin antigen) and IgG2a mg/ml (Th1 response—cell-mediated immunity to the ovalbumin antigen) were measured by ELISA.

Figure 1:
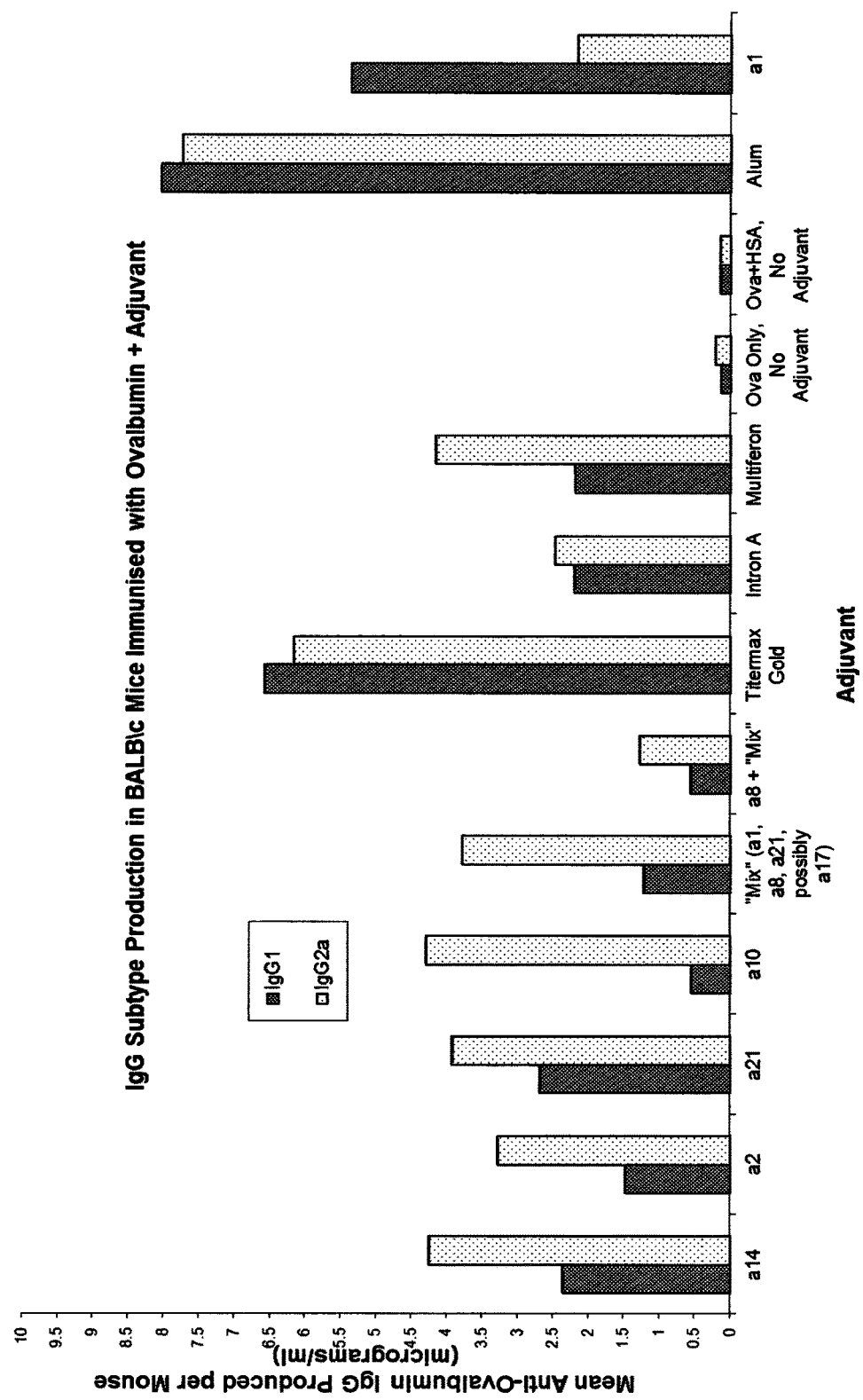
FIG. 1 shows a graph of IgG subtype (IgG1 and IgG2a) production in BALB-c mice immunised with ovalbumin and different subtypes of IFN-α.
Figure 2:
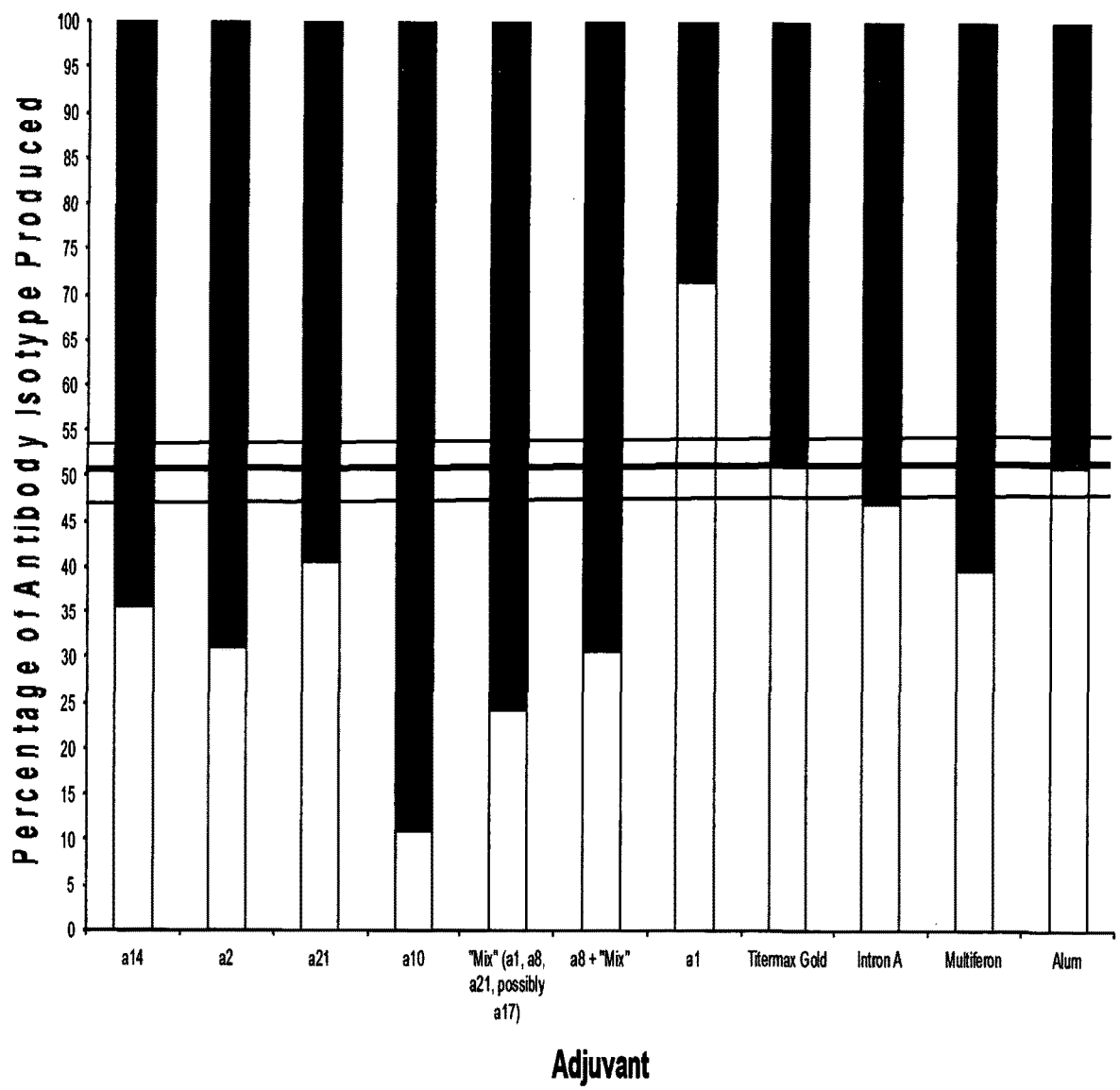
FIG. 2 shows a graph of the percentage of IgG subtype (IgG1 and IgG2a) produced in BALB-c mice immunised with ovalbumin and different subtypes of IFN-α.
Figure 3:
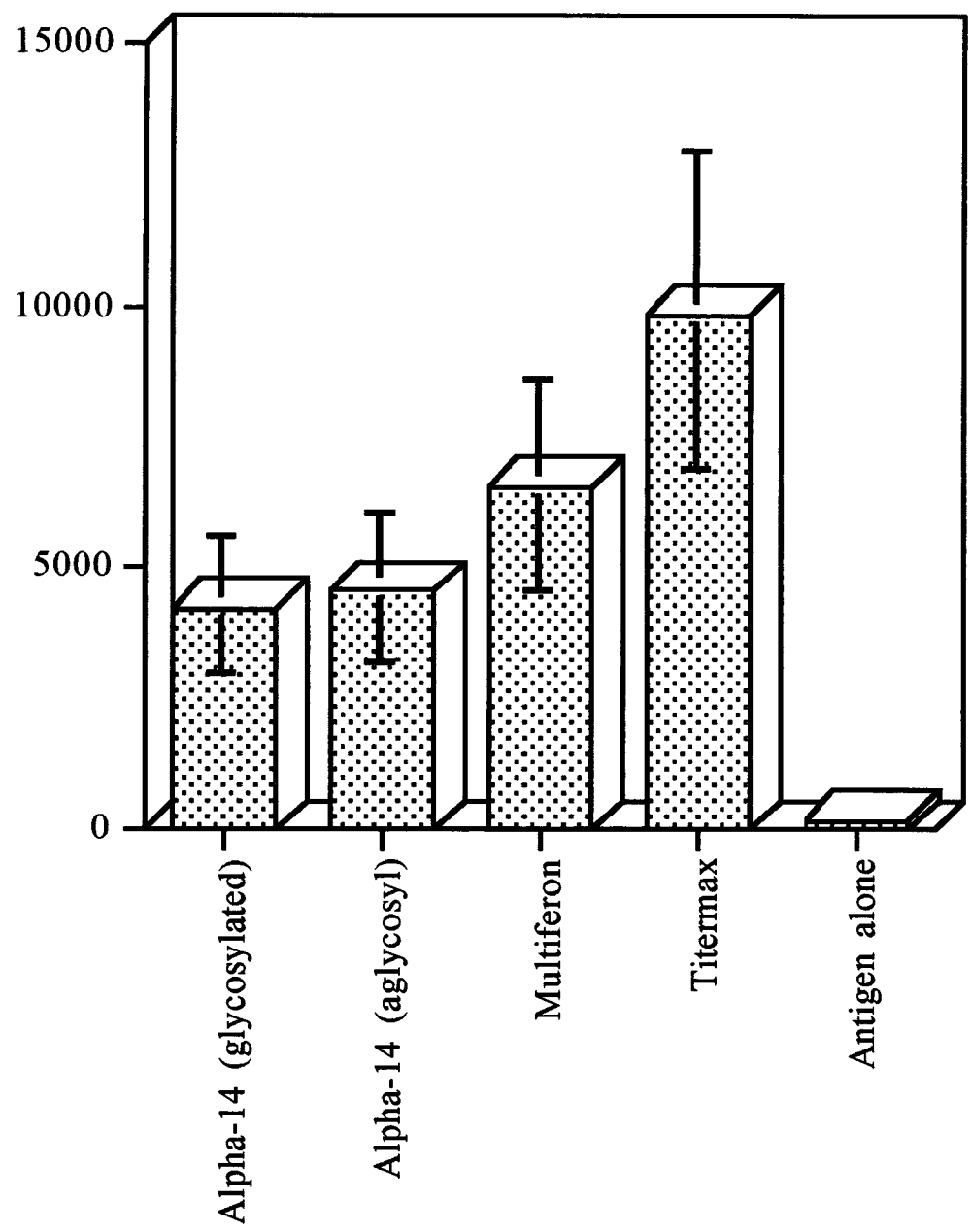
FIG. 3 shows a graph of IgG2a production in BALB-c mice immunised with ovalbumin and MULTIFERON™, glycosylated IFN-α14 and non-glycosylated IFN-α14 administered via intraperitoneal injection.
Figure 4:
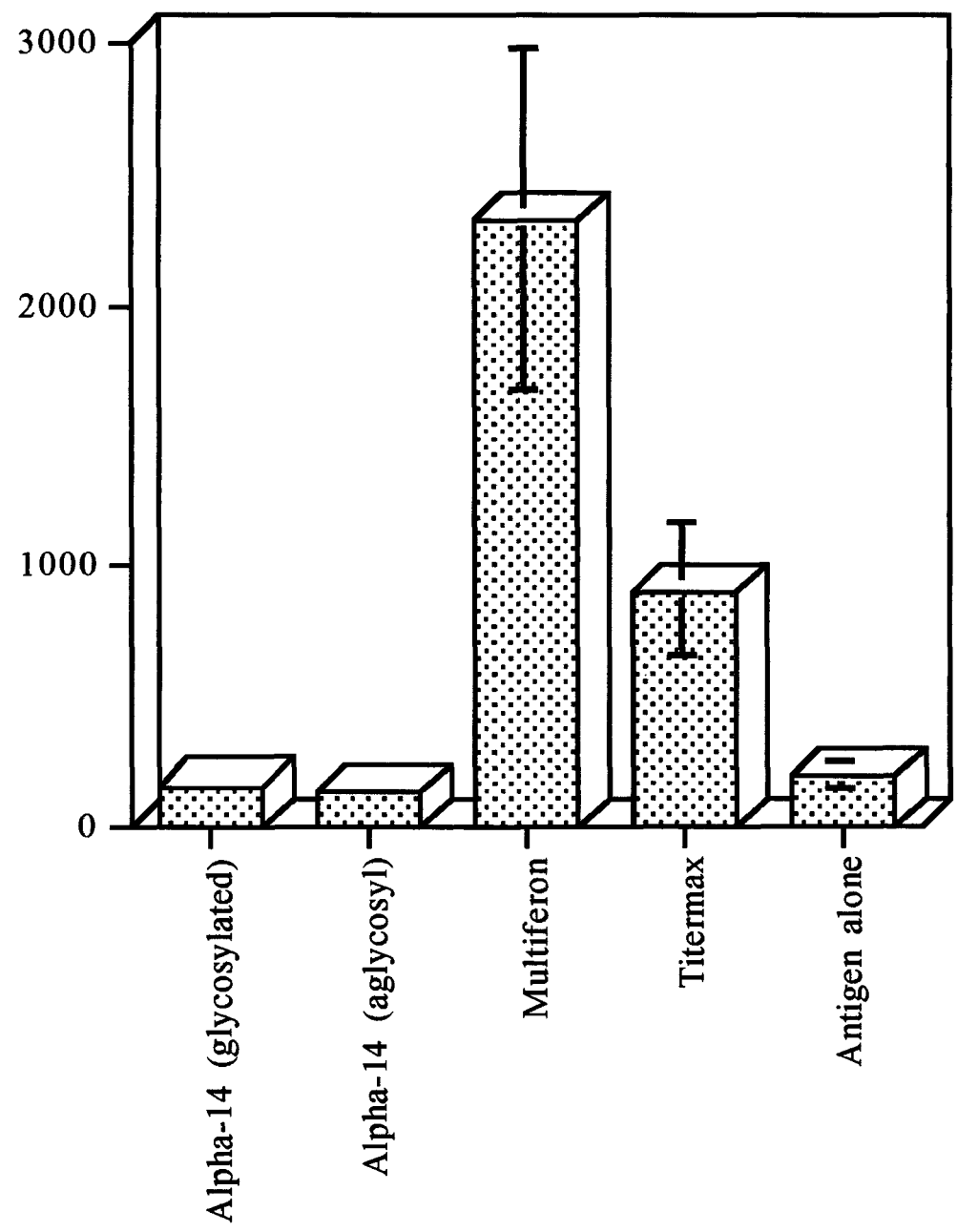
FIG. 4 shows a graph of IgG1 production in BALB-c mice immunised with ovalbumin and MULTIFERON™, glycosylated IFN-α14 and non-glycosylated IFN-α14 administered via intraperitoneal injection.
Figure 5:
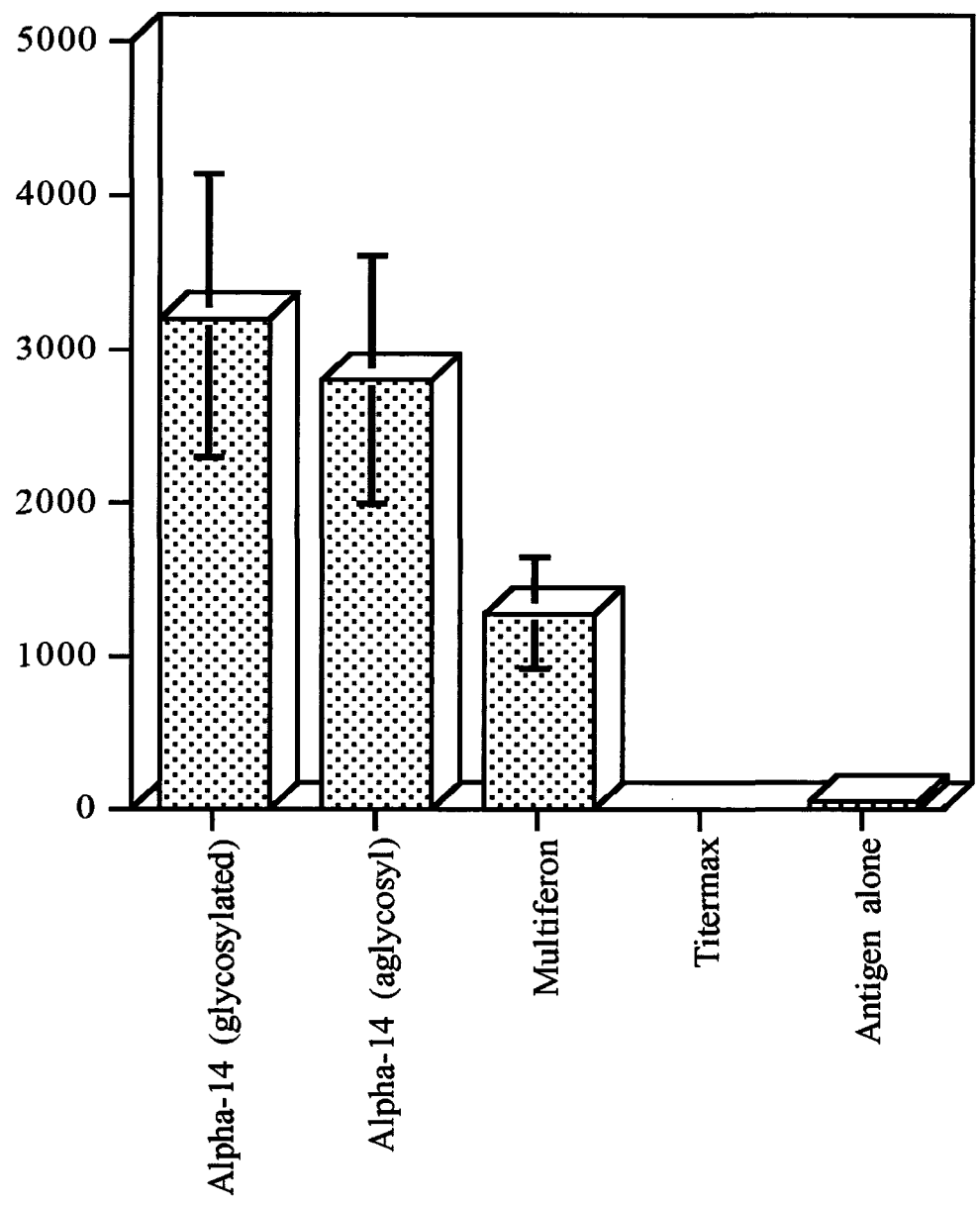
FIG. 5 shows a graph of IgG2a production in BALB-c mice immunised with ovalbumin and MULTIFERON™, glycosylated IFN-α14 and non-glycosylated IFN-α14 administered orally.
Figure 6:
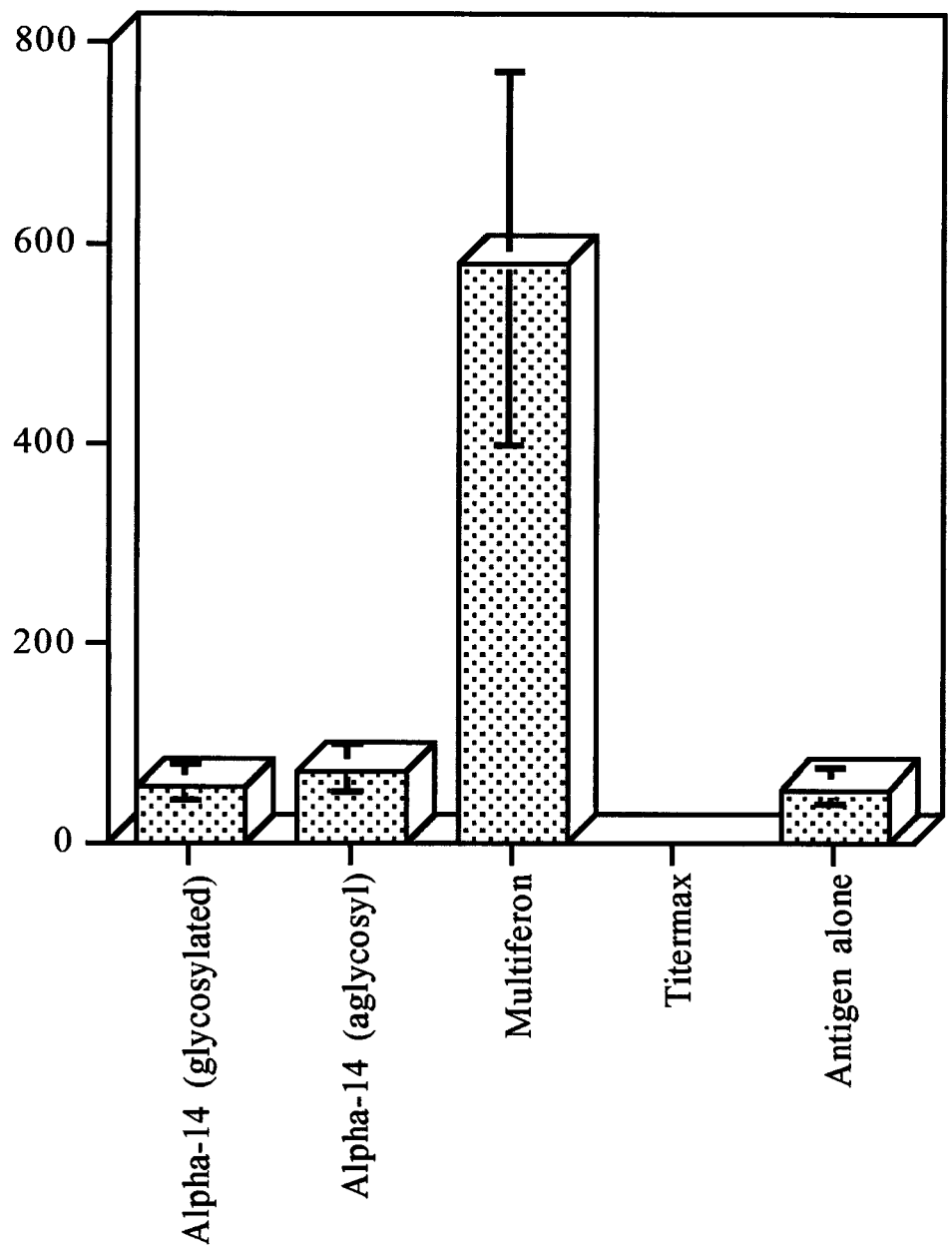
FIG. 6 shows a graph of IgG1 production in BALB-c mice immunised with ovalbumin and MULTIFERON™, glycosylated IFN-α14 and non-glycosylated IFN-α14 administered orally.

FIGS. 1 and 2 show the anti-ovalbumin IgG subtype production in BALB-c mice treated with IFN-α14, IFN-α2, INF-α21, IFN-α10, a "mix" of IFN-α1, IFN-α8, IFN-α21 and possibly IFN-α17), IFN-α8, Intron A, MULTIFERON™, ovalbumin only, ovalbumin plus human serum albumin (used as a carrier in interferon preparations) and IFN-α1.

The inventor demonstrated that IFN-α10 and IFN-α14 enhanced the production of IgG2a antibodies significantly which is indicative of an enhanced Th1 immune response. The inventor also demonstrated that IFN-α10 in particular showed low production of IgG1 antibody which is indicative of suppressing a Th2/Th17 immune response.

EXAMPLE 2

Identification of Antibody Response in BALB-c Mice After Administration of a Composition Comprising a Flu Vaccine and a Low Dose of Leukocyte Derived Interferon-Alpha (LDA1)

The standard flu vaccine was mixed with a low dose ($10^5$ IU) of leukocyte derived interferon alpha (LDA1). Without the interferon, a small anti-flu antibody response was recorded in mice, approximately 50 times less than with an injection. With interferon-alpha, the response from the orally delivered vaccine was exactly the same as the injected vaccine. A series of buccal immunisations were carried out using a standard protein antigen (ovalbumin). Two interferons were compared, namely, the LDA1 and an isolated subtype, IFN-α14. Both produced a remarkable oral immunisation of the mice, but whereas the LDA1 gave a balanced response, the IFN-α14 gave only a significant humoral response. The production of IgG1 is indicative of a Th2/Th17 response (humoral immunity) and the production of IgG2a is indicative of a Th1 response (cell-mediated immunity).

EXAMPLE 3

The Identification of IFN-Alpha as an Oral Immunological Adjuvant

50 µg ovalbumin and $10^5$ IU of interferon subtypes, namely MULTIFERON™, glycosylated IFN-α14 and non-glycosylated IFN-α14, in 50 µl doses were administered three times a week to BALB-c female mice via oral (buccal) and intraperitoneal injection administration.

The controls used were antigen alone and Titermax—Titermax is a mixture of compounds used in antibody generation and vaccination to stimulate the immune system to recognise an antigen given together with the mixture. Titermax is a recently developed immune adjuvant deemed to be safe in animals.

Serum concentrations (mg/ml) of IgG1 (indicative of a Th2/Th17 response) and IgG2a (indicative of a Th1 response) anti-ovalbumin antibodies were quantitated by ELISA.

The production of IgG2a and IgG1 antibodies when MULTIFERON™, glycosylated IFN-α14 and aglycosyl IFN-α14 (CHO cell-derived) were administered both orally and by injection were compared (see FIGS. 3, 4, 5 and 6).

The inventor demonstrated that IFN-α14 showed pronounced immunological adjuvant activity both orally and by injection. No significant difference was seen between the glycosylated and non-glycosylated preparations.

The inventor also demonstrated that IFN-α14 only enhanced IgG2a production associated with Th1 responses by the oral route of administration. Hence IFN-α14 is an activator of cell-mediated immunity when administered orally.

MULTIFERON™ enhanced both IgG1 and IgG2a responses when administered both orally and by injection i.e. it induced both Th1 and Th2 responses significantly.

EXAMPLE 4

In Vitro Determination of the Inhibition of Humoral Immunity (Th2/Th17) by Interferon-Alpha Subtypes—Analysis of Th17 Lymphocytes and Interleukin 17

A total of $2 \times 10^6$ human PBMCs were stimulated with lipopolysaccharide (LPS) in the absence or presence of increasing concentrations of recombinant human alpha-IFN. Supernatants were collected after 24 hours and IL-17 concentrations measured by ELISA.

Human Cell Culture

Human peripheral blood was collected from healthy volunteers and peripheral blood mononuclear cells (PBMCs) were obtained by Lymphoprep gradient centrifugation (Pierce). For PBMC experiments, $2 \times 10^6$ PBMCs per ml were seeded in 24-well plates and stimulated with lipopolysaccharide (LPS) from *Escherichia coli* 055:B5 (Sigma) or $2 \times 10^6$ PBMCs per mL were seeded into 24-well plates and stimulated with 5 mg/mL plate-bound anti-CD3 (clone: UCHT1) and 2.5 mg/ml. anti-CD28 (clone: CD28.2). Naive T cells (CD4+CD45RA) were obtained by magnetically labeling and depletion of non-helper T-cell and memory T-cells performed according to manufacturer's instructions (Miltenyi Biotec). A total of 1×10$^5$ naive T-cells were primed in 96-well flat bottom plates coated with anti-CD3 (clone UCHT1, 2.5 mg/mL) and with anti-CD28 (clone CD28.2, 2.5 mg/mL) antibodies. After 48 h of culture, 20 IU/mL recombinant human IL-2 (Peprotech) was added to the culture.

For human Th17 differentiation, cells were supplemented with neutralising anti-IL-4 and anti-IFNγ antibodies (both from Peprotech) and with 10 ng/mL recombinant IL-1β and 50 ng/mL recombinant IL-6 (both from Peprotech). Where required, recombinant human IFNα10/14 was added to the culture. After 5 days of culture, cells were washed, transferred into new plates and expanded until day 12 in the presence of 20 IU/mL recombinant IL-2.

ELISA and Intracellular Cytokine Staining

The IL-17 producing capacity of primed Th17 cells was assessed by stimulation with 0.1 ng/ml LPS or alternatively can be assessed by the stimulation of human cells with soluble 1 mg/mL anti-CD3 (clone: OKT3) and phorbol-12-13-dibutyrate (PdBu). Concentrations of human IL-17 in cell culture supernatants were determined using commercially available antibody pairs and protein standards (R&D Systems). Absorption was determined using an ELISA reader at 450 nm. For intracellular staining of mouse IFNγ and IL-17, T-cells are stimulated with PMA and ionomycin for 5 hours. Brefeldin A is added for the final 3 h of culture. Intracellular staining can be performed with a BD Cytofix/Cytoperm kit according to the manufacturer's instructions. Cells are incubated with fluorescein isothiocyanate-labeled anti-IFNγ (clone: XMG1.2, BD Pharmingen) and Alexa Fluor 647-labeled anti-mouse mouse IL-17A (clone: eBio17B7, eBioscience). After washing, cells are immediately analysed using Fluorescence-activated cell sorting (FACS).

Results

Figure 7:
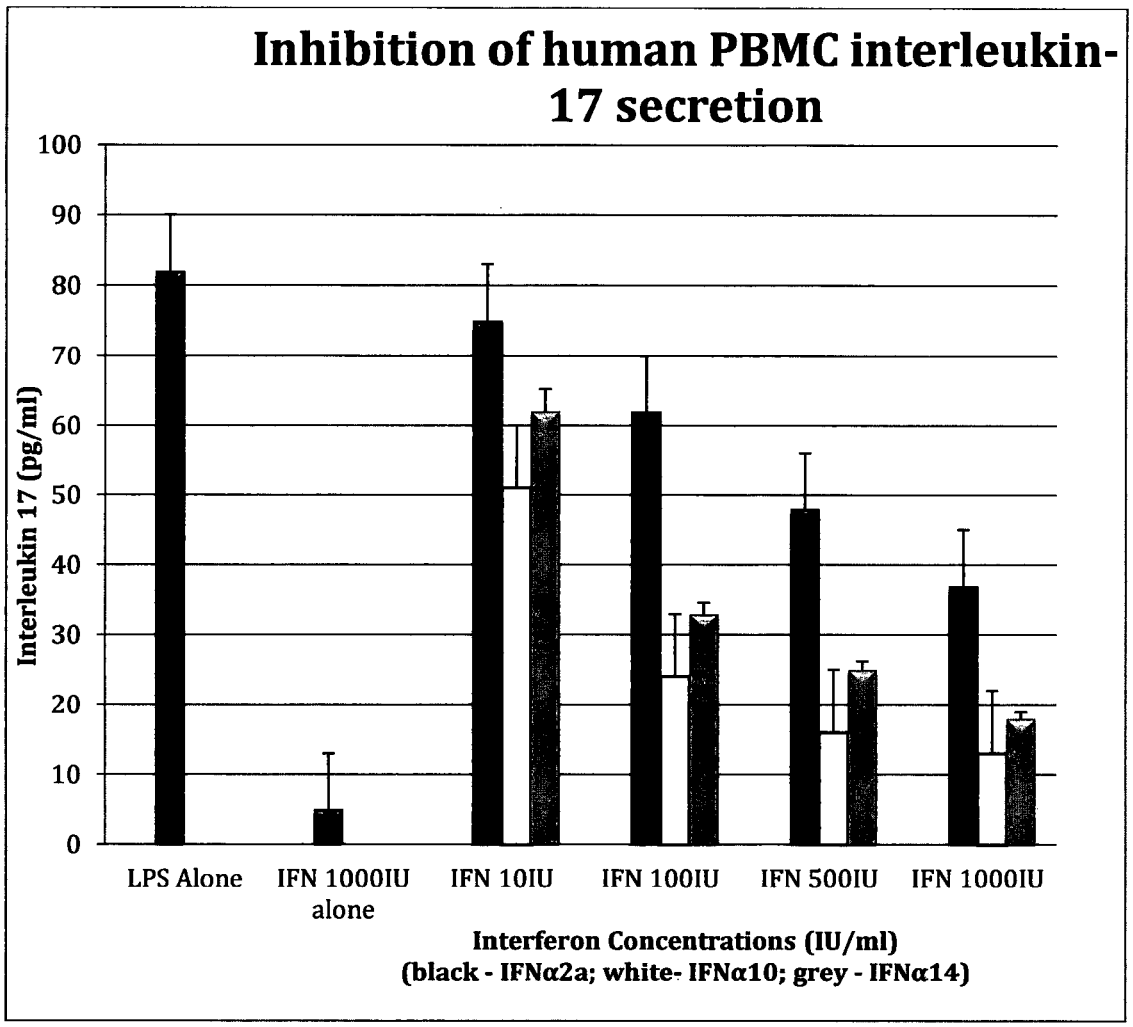
FIG. 7 shows inhibition of human PBMC interleukin-17 (IL-17) secretion with lipopolysaccharide (LPS) alone and with LPS and increasing concentrations of IFN-α2a (black), IFN-α10 (white) or IFN-14 (grey).

As shown by FIG. 7, inhibition of IL-17 was found to occur in the order IFNα10>IFNα14>IFNα2a. P<0.05 (FIG. 7).

EXAMPLE 5

In Vitro Determination of the Inhibition of Humoral Immunity Th2/Th17) by Interferon-Alpha Subtypes—Analysis of Th2 Cells and Associated Cytokines CRTH2 Background CRTH2 (Chemoattractant Receptor-homologous molecule expressed on Th2 cells) is a G-protein coupled receptor expressed by Th2 lymphocytes, eosinophils, and basophils. The receptor mediates the activation and chemotaxis of these cell types in response to prostaglandin D2 (PGD2), the major prostanoid produced by mast cells. PGD2 is released through mast cell degranulation in the initial phase of IgE-mediated reactions. This process is also thought to occur at the site of inflammation, such as the nasal and bronchial mucosa. Through interaction with CRTH2, PGD2 is thought to mediate recruitment and activation of CRTH2-bearing cell types to the site of the allergic reaction, in consequence amplifying and maintaining the allergic inflammation. In the nasal and bronchial mucosa, this pro-inflammatory cascade is thought to start during the so-called late allergic response occurring 3 to 9 hours after allergen challenge. The interaction between PGD2 and CRTH2 would, therefore, contribute to the so-called "Th2 polarisation", with consequent Th2 cytokine production and the typical eosinophilic and basophilic characteristics of the inflammation.

IFNα Inhibits Human CD4+ Th2 Development

Purified human CD4+/CD45RA+ cells were activated with plate-bound anti-CD3/anti-CD28 under defined cytokine conditions. Induction of CRTH2 expression was assessed by flow cytometry. All P<0.05, above 100 IU IFN compared with IL-4alone.

Human Subjects

Peripheral blood was collected from healthy adult donors and cells purified as below.

T Cell Cultures and Analysis

Peripheral blood was obtained from healthy male adult donors and naive CD4+/CD45RA+ T cells were purified (>92%) from buffy coats by magnetic bead separation (BD Biosciences, USA). CD4+ cells were activated with plate-bound anti-CD3/anti-CD28 and IL-2 (50 U/ml) in complete Iscove's Modified Dulbecco's Medium containing 10% FCS, in the presence of recombinant human recombinant IL-4 (R&D Systems, USA), at a concentration of 20 ng/ml for 7 days. Flow cytometric analysis was performed with hCD294 (chemo-attractant receptor homologous molecule expressed on Th2 cells [CRTH2])-Alexa 647 (BD Biosciences).

Results

Figure 8:
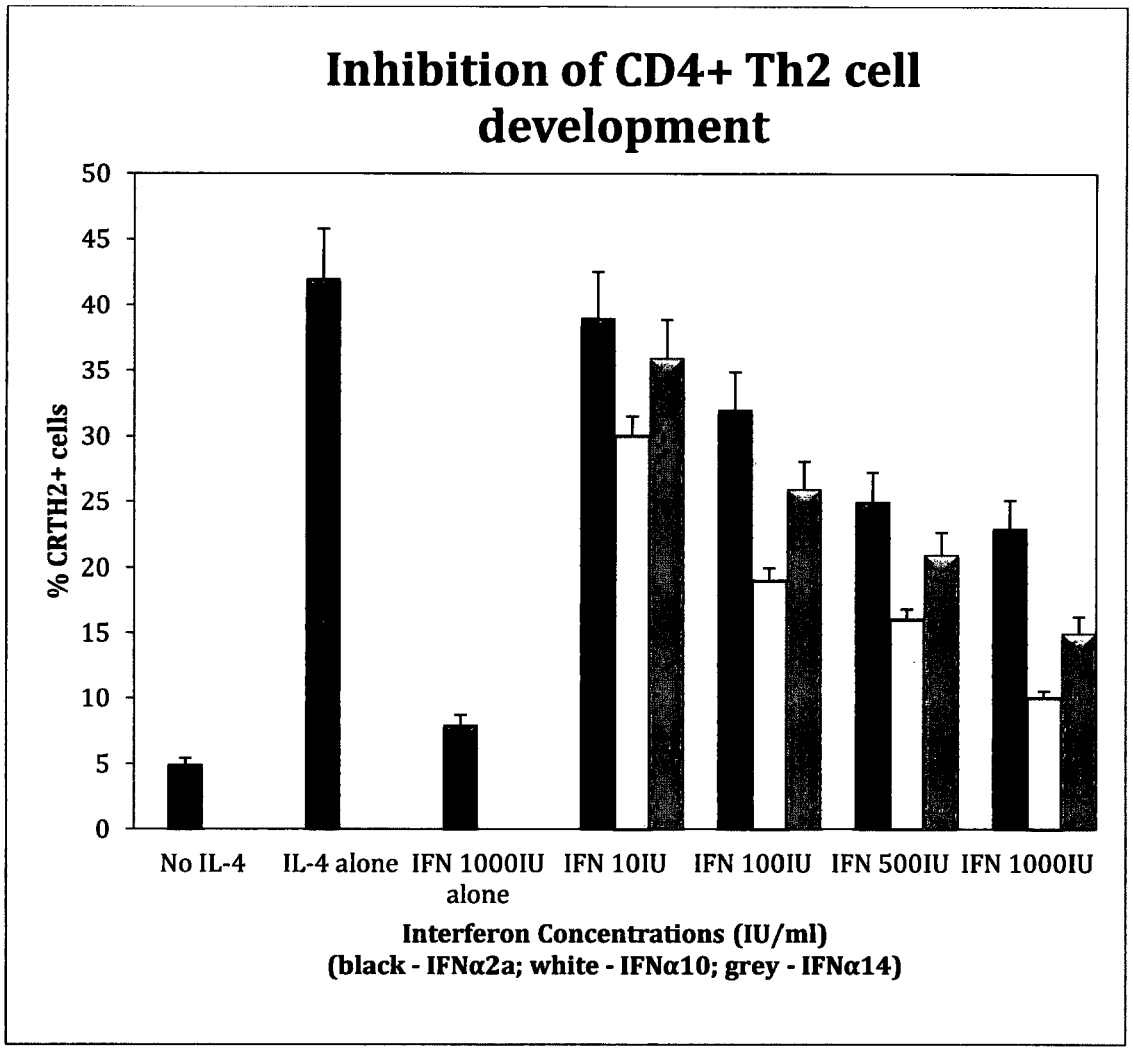
FIG. 8 shows the inhibition of Interleukin-4 (IL4)-induced CD4+ Th2 cell development using increasing concentrations of IFN-α2a (black), IFN-α10 (white) or IFN-14 (grey).
Figure 11:
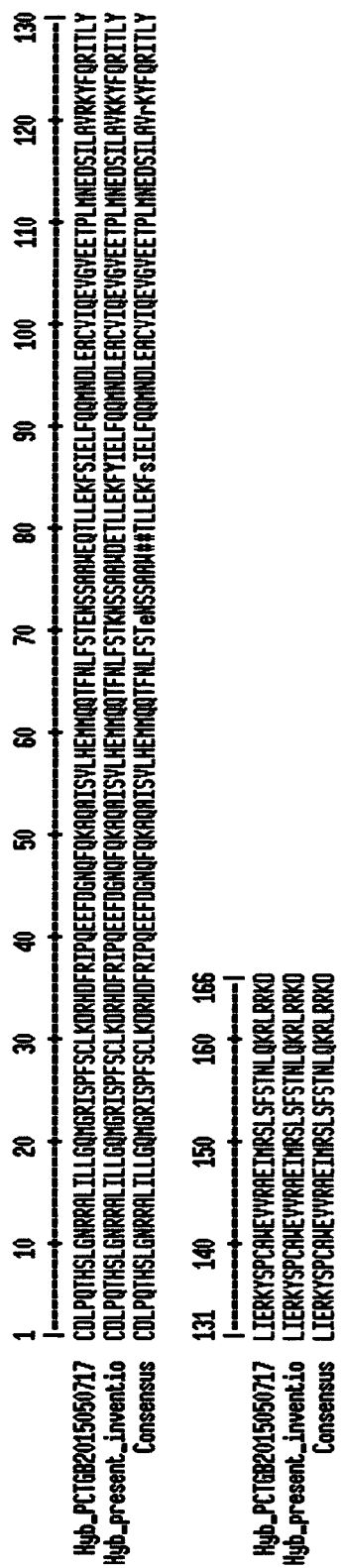
FIG. 11 shows the alignment of a previously described IFNalpha10 and IFNalpha14 hybrid amino acid sequence (SEQ ID NO:3) with the IFNalpha10 and IFNalpha14 hybrid amino acid sequence as presently claimed (SEQ ID NO: 1).

In humans, the PGD2 receptor, CRTH2, is selectively expressed on Th2 cells and is induced by IL-4 during Th2 development. IL-4 promoted the development of cells expressing CRTH2. However, as shown in FIG. 8 all the IFN-alphas markedly blocked IL-4 driven CRTH2 expression, in a dose-dependent manner in the order IFNα10>IFNα14>IFNα2a, thus supporting the concept that these cytokines suppress Th2 (humoral) immunity, but are recognised as potent activators of Th1-associated immunity.

Figure 12:
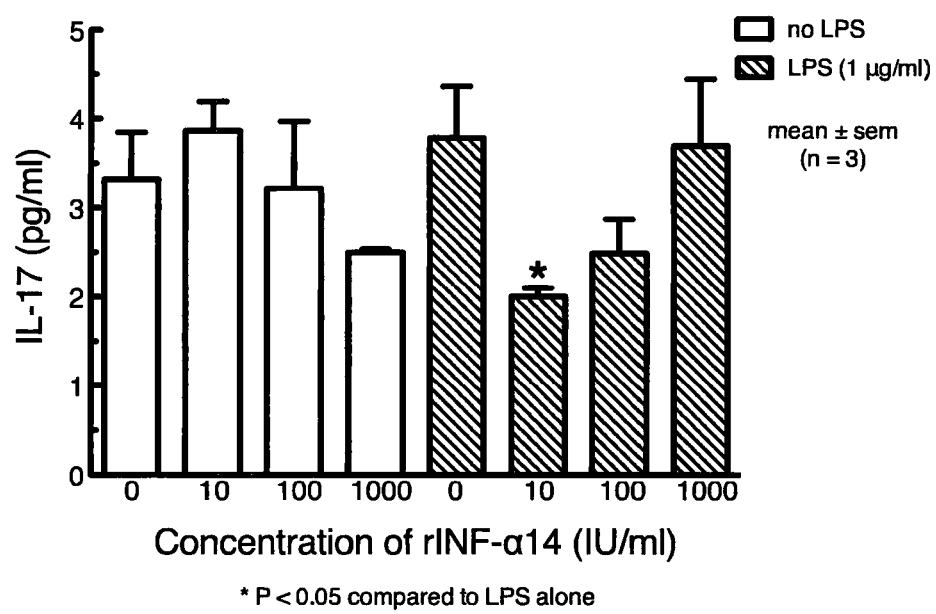
FIG. 12 indicates the effect caused by rIFN-α14 on the production of IL-17 in whole human blood incubated with one microgram E.coli lipopopolysaccharide (LPS) for 48 hours. The α-14 gave a significant suppression of IL-17 secretion. IL-α-2 and α-10 showed no significant suppression.

As shown in FIG. 12, the effect of rIFN-α14 on the production of IL-17 in human blood incubated with LPS for 48 h was tested.

Whole human blood was incubated without (open columns) or with 1 μg/ml LPS (cross hatched columns) in the absence and presence of a range of concentrations of rIFN-α14 (0–1,000 IU/ml) for 48 h at 37° C., in an atmosphere of 5% CO2 in air, in a humidified incubator. Plasma was collected by centrifugation and levels of IL-17 determined by ELISA.

FIG. 12 indicated a dose response to IFN-α14 wherein 1 mg=10$^{-8}$ IU.

Figure 13:
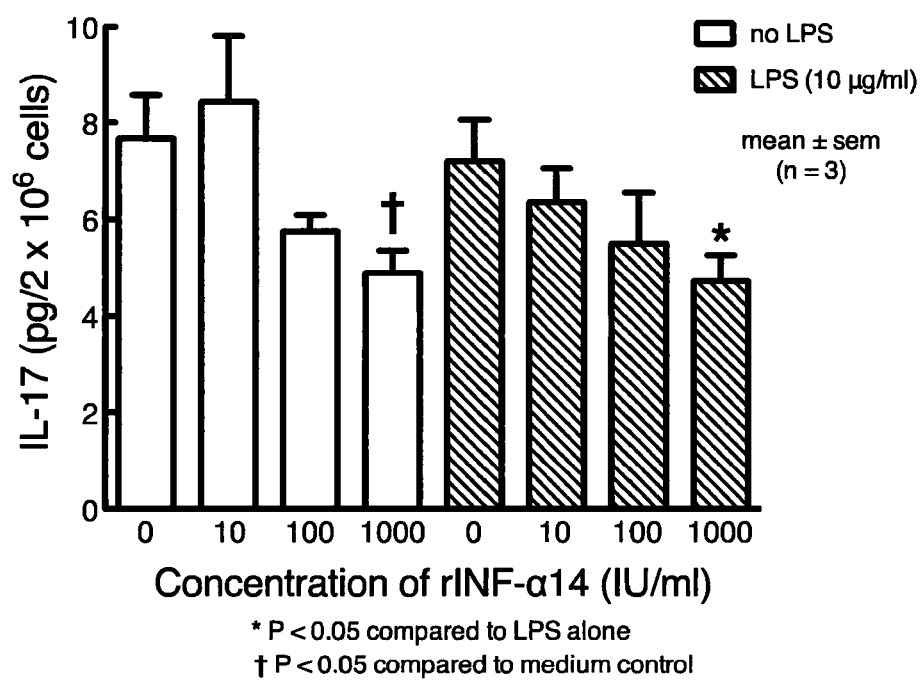
FIG. 13 shows the effect caused by rIFN-α14 on the production of IL-17 from human peripheral blood mononuclear cells incubated with 10 micrograms *E. coli* lipopolysaccharide (LPS) for 48 hours. The α-14 caused a significant suppression of IL-17 secretion with and without LPS activation. IL- α-2 and α-10 showed no significant changes in the IL-17 concentrations (results not shown).

As shown in FIG. 13 the effect of rIFN-α14 on the production of IL-17 in human PBMCs incubated with LPS for 48 h was tested.

Human Peripheral Blood Mononuclear cells (PBMCs), a critical component in the immune system, were isolated from whole human blood by density gradient centrifugation. 2×10$^6$ PBMCs were incubated without (open columns) or with 10 μg/ml LPS (cross hatched columns) in the absence and presence of a range of concentrations of rIFN-α14 (0–1,000 IU/ml) for 48 h at 37° C., in an atmosphere of 5% CO2 in air, in a humidified incubator. Levels of IL-17 in the supernatant were determined by ELISA.

As indicated by FIG. 13, increasing concentrations of rIFN-α14 was found to reduce the IL-17 both in untreated and treated LPS cells.

Figure 14:
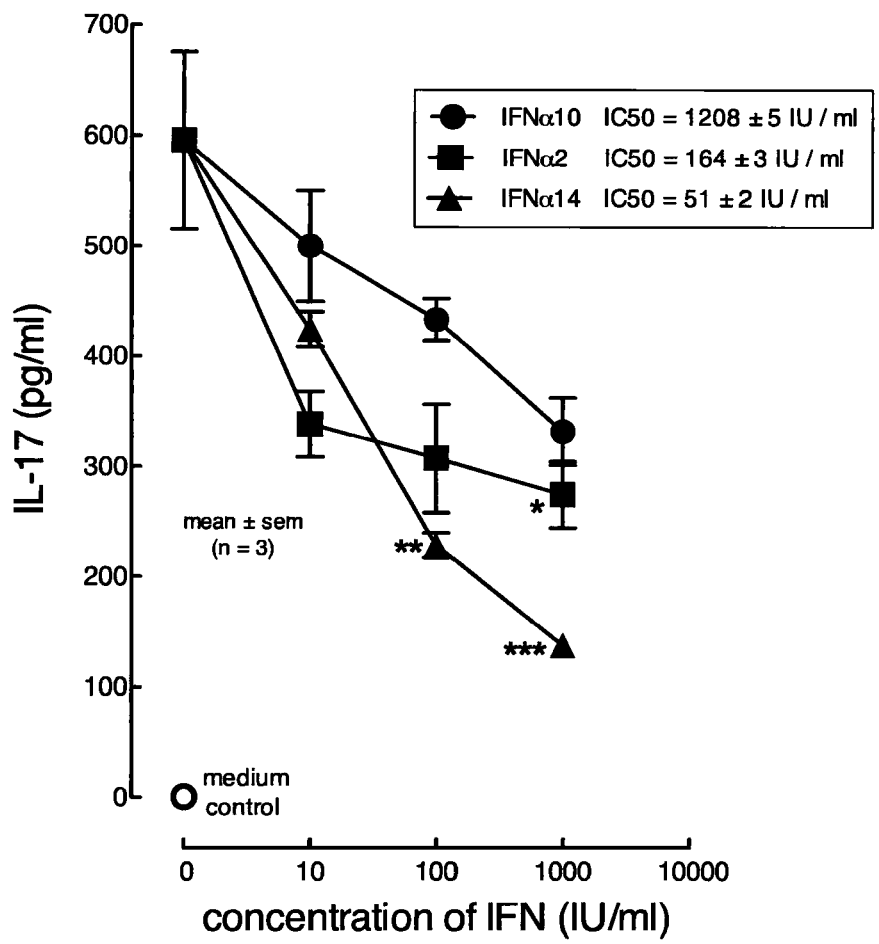
FIG. 14 shows the effect caused by rIFN-α10, rIFN-α14 and rIFN-α2 on IL-17 production by whole human blood incubated with PHA for 5 days. The α-14 is an extremely potent inhibitor (P<0.001 at 1,000 IU/ml) of IL-17 compared with the commonly available α-2; the α-10 is more than 20× less active in this context

As shown in FIG. 14, the effect of rIFNα10, rIFNα14 and rIFN2 on IL-17 production by whole blood incubated with phytohaemagglutinin (PHA) for 5 days was tested.

Whole human blood was diluted 1/10 with RPMI 1640 culture medium and incubated without or with 100 μg/ml PHA in the absence and presence of a range of concentrations of rIFN-α14, rIFN-α10 and rIFN-α2 for 5 days at 37° C., in an atmosphere of 5% CO2 in air, in a humidified incubator. At the end of this period, supernatants were aspirated and levels of IL-17 in supernatants measured by ELISA. Values represent the mean ± sem, for n=3 incubations. Statistical analysis and $IC_{50}$ values were determined using GraphPad Prism 5 (GraphPad Software Inc., California, USA).

As indicated in FIG. 14 the provision of rIFN-α14 at higher concentrations (100-1000 IU/ml) caused a greater decrease in IL-17 than the provision of IFN-α2 or IFN-α10. rIFN-α14 is considered to be the most potent interferon tested at reducing IL-17 levels.

Figure 17:
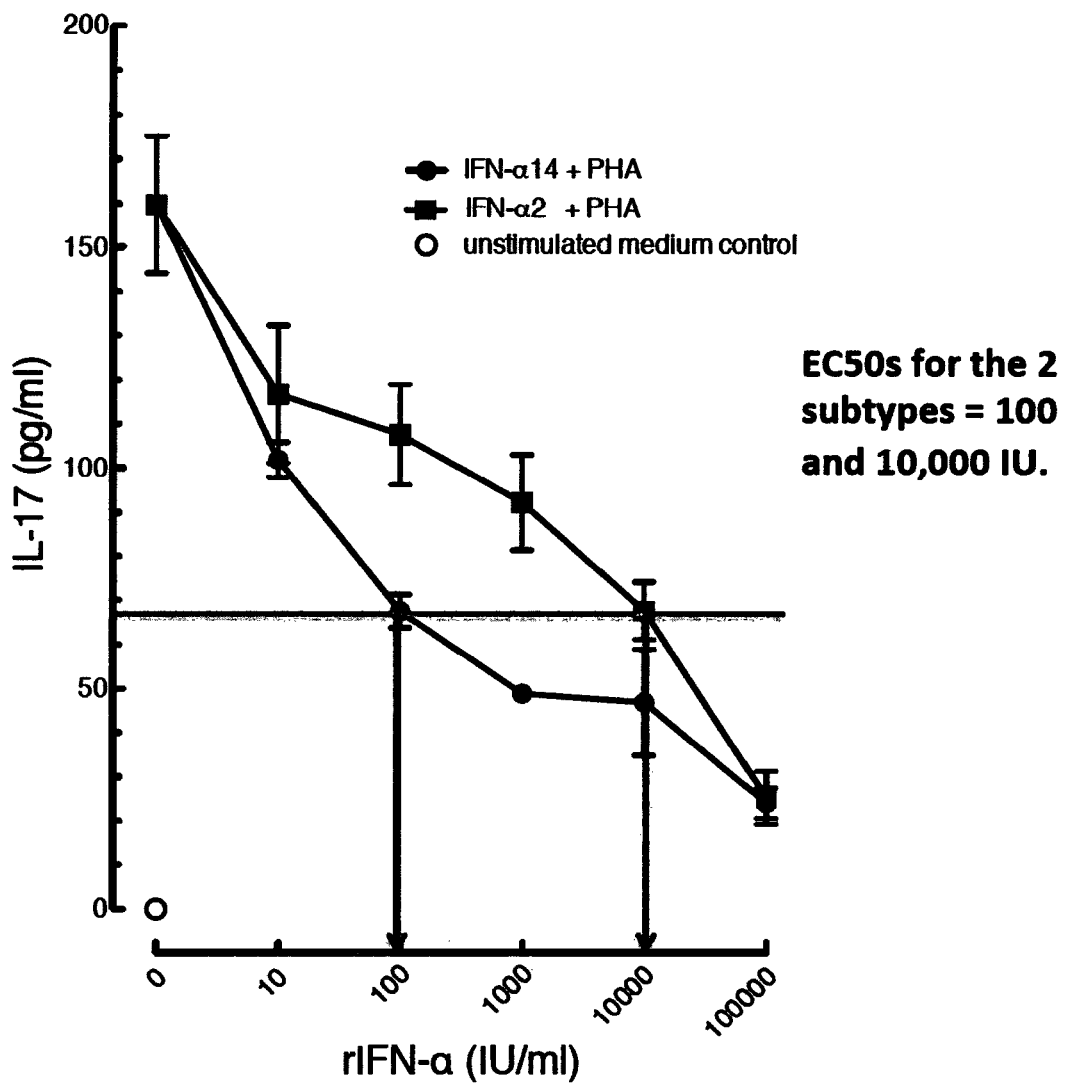
FIG. 17 shows the effect caused by rIFN-α14 and rIFN-α2 on IL-17 production by whole human blood incubated with PHA for 5 days. The α-14 is an extremely potent inhibitor of IL-17 compared with the commonly available IFN-α2 (EC50s for the two subtypes are 100 and 10,000 IU/ml).

Similar results were achieved as shown in FIG. 17. Here the effect of rIFNα14 and rIFN2 on IL-17 production by whole blood incubated with phytohaemagglutinin (PHA) for 5 days was tested using the same methodology. As indicated in FIG. 17 the provision of rIFN-α14 at higher concentrations (100-1000 IU/ml) caused a greater decrease in IL-17 than the provision of IFN-α2. rIFN-α14 is considered to be the most potent interferon tested at reducing IL-17 levels.

Figure 15:
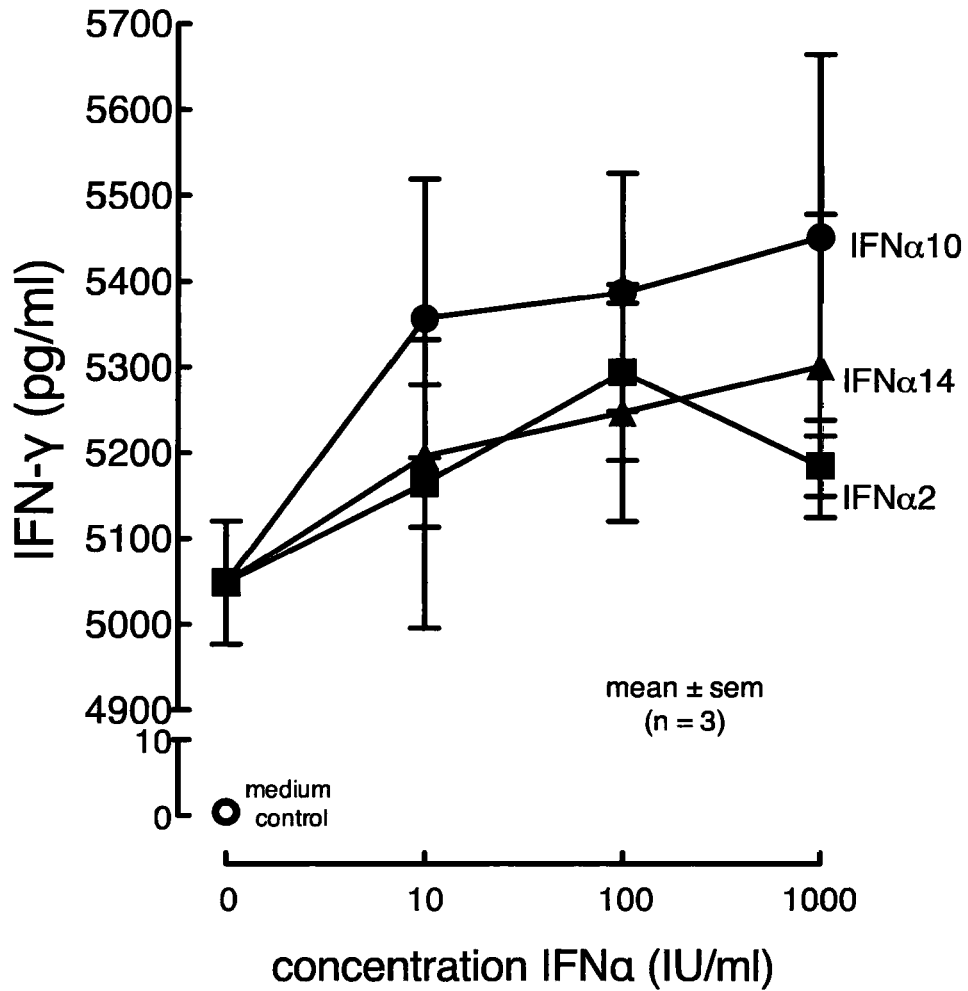
FIG. 15 shows the effect caused by rIFN-α10, rIFN-α14 and rIFN-α2 on IFN-gamma production by whole human blood incubated with PHA for 5 days. The α-10 is the most potent interferon—alpha in this context causing enhanced secretion of IFN-gamma—critical for both and innate and adaptive immunity against viruses, intracellular bacterial infections and in the control/elimination of tumours.
Figure 16:
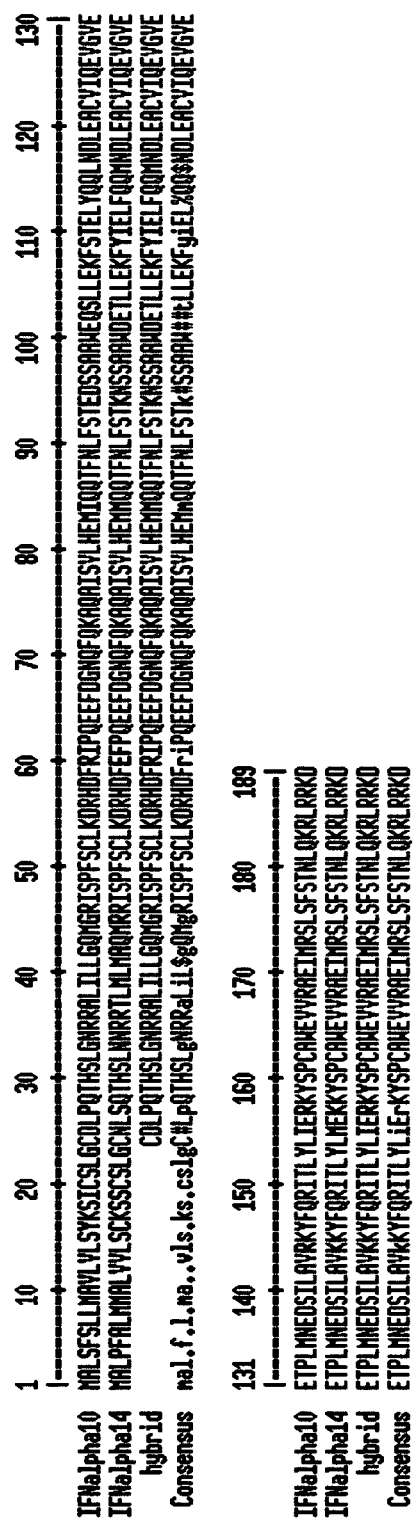
FIG. 16 illustrate a sequence alignment of IFN-alpha10 (SEQ ID NO:4) and IFN-alpha14 (SEQ ID NO:5) amino acid sequences and the hybrid sequence SEQ ID NO: 1 discussed herein.

As shown in FIG. 15, the effect of rIFNα10, rIFNα14 and rIFNα2 on IFN-gamma production by whole blood incubated with PHA for 5 days.

Whole human blood was diluted 1/10 with RPMI 1640 culture medium and incubated without or with 100 μg/ml PHA in the absence and presence of a range of concentrations of rIFN-α10, rIFN-α14 and rIFN-α2 for 5 days at 37° C., in an atmosphere of 5% $CO_2$ in air, in a humidified incubator. At the end of this period supernatants were aspirated and levels of IFN-gamma in supernatants measured by ELISA. Values represent the mean ± sem, for n=3 incubations, plasma was collected by centrifugation and levels of IFN-gamma determined by ELISA. Values represent the mean ± sem, for n=3 incubations.

It was determined that rIFN-α10 was the most effective of the interferons tested at promoting levels of IFN-gamma. IFN-gamma has previously been suggested to be important in providing an anti-cancer effect.

Figure 18:
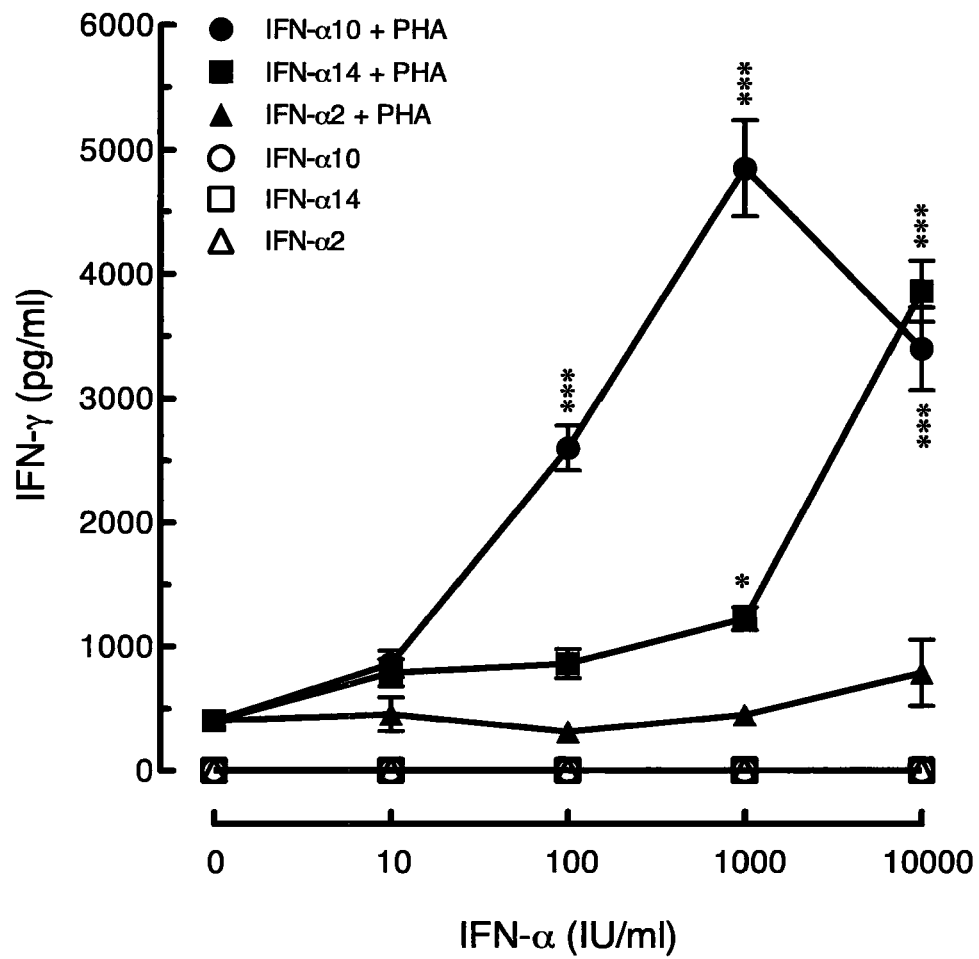
FIG. 18 shows the induction of Interferon-gamma by Interferon-alpha subtypes and in particular demonstrates the effect caused by IFN-α10, IFN-α14 and IFN-α2 on IFN-gamma production by whole human blood incubated with PHA for 5 days. The α-10 is the most potent interferon—alpha in this context causing enhanced secretion of IFN-gamma.

Similar results were achieved as shown in FIG. 18. Here the effect of rIFNα14 and rIFN2 on IFN-gamma production by whole blood incubated with phytohaemagglutinin (PHA) for 5 days was tested using the same methodology. As indicated in FIG. 18 the provision of rIFN-α10 caused a greater increase in IFN-gamma than the provision of IFN-α2. rIFN-α10 is considered to be the most potent interferon tested at increasing IFN-gamma levels.

Figure 19:
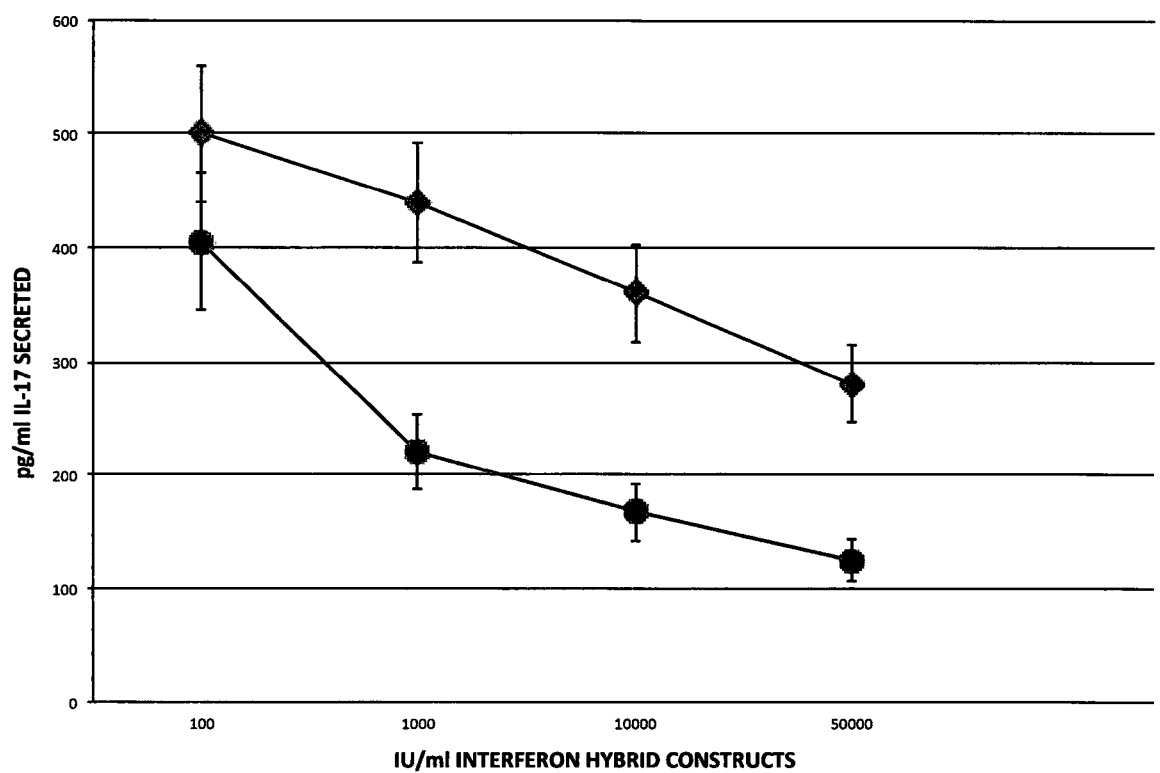
FIG. 19 shows the effect of the IFN-α10-IFN-α14 hybrid of the present invention (SEQ ID NO:1) on IL-17 production from whole human blood compared to the effect on IL-17 of a previously disclosed IFN-α10-IFN-α14 hybrid. The hybrid of the present invention demonstrates an greater reduction in IL-17.

As shown in FIG. 19, the effect of the IFN-α10-IFN-α14 hybrid of the present invention (SEQ ID NO:1) on IL-17 production from whole human blood was compared to the effect on IL-17 of the IFN-α10-IFN-α14 hybrid disclosed in PCT/GB2015/050717.

Whole human blood was diluted 1/10 with RPMI 1640 culture medium and was incubated with PHA (100 μg/ml) in the presence of a range of concentrations of either the IFN-α10-IFN-α14 hybrid of the present invention (IFN alpha-hybrid 1) or the IFN-α10-IFN-α14 hybrid disclosed in PCT/GB2015/050717 (IFN alpha-hybrid 2) for 5 days at 37° C. in an atmosphere of 5% C02 in air in a humidified incubator. At the end of this period supernatants were collected and levels of IL-17 measured by ELISA. Values represent mean ± sem, for n=3 incubations. P<0.05 for all points of the data between the two hybrids except 100 IU/ml, which was non significant The Red diamonds indicate IFN-α10-IFN-α14 hybrid 1 and the blue circles indicate IFN-α10-IFN-α14 hybrid 2.

It was determined that the IFN-α10-IFN-α14 hybrid of the present invention demonstrates a greater reduction in IL-17.

EXAMPLE 6

Effects of Human Interferon Alpha-14 and Alpha-10 on Unstimulated and Activated Human Mononuclear Leukocytes from Normal Subjects

TABLE 1

Synopsis of 400 interleukins, chemokines, and protein markers estimations* following IFN-α10/14 treatment of human mononuclear cells

| ANALYTE | FOLD NUMBER OF UNSTIMULATED/ ALPHA-IFN TREATED CELLS | | FOLD NUMBER OF PHA-STIMULATED/PHA-STIMULATED ALPHA-IFN TREATED CELLS | |
|---|---|---|---|---|
| CYTOKINES | Alpha-14 | Alpha-10 | Alpha 14 | Alpha 10 |
| IL-1a | 0 | +23 | 1 | +2 |
| IL-1b | 0 | +70 | −2 | 1 |
| IL-1(F5 to F10) | 0 | 0 | 0 | 0 |
| IL-2 | 0 | 0 | +7 | +4 |
| IL-3 | 0 | 0 | −11 | x |
| IL-4 | 0 | 0 | 1 | −3 |
| IL-5 | 0 | 0 | −420 | 1 |
| IL-6 | −19 | +1000 | 1 | 1 |
| IL-7 | 0 | 0 | 0 | 0 |
| IL-8 | 1 | +100 | 1 | 1 |
| IL-9 | 0 | 0 | 0 | 0 |
| IL-10 | 0 | +5 | +2 | +2 |
| IL-11 | 0 | 0 | 0 | 0 |

TABLE 1-continued

Synopsis of 400 interleukins, chemokines, and protein markers estimations* following IFN-α10/14 treatment of human mononuclear cells

| ANALYTE | FOLD NUMBER OF UNSTIMULATED/ ALPHA-IFN TREATED CELLS | | FOLD NUMBER OF PHA-STIMULATED/PHA-STIMULATED ALPHA-IFN TREATED CELLS | |
|---|---|---|---|---|
| CYTOKINES | Alpha-14 | Alpha-10 | Alpha 14 | Alpha 10 |
| IL-12 p40 | 0 | +350 | 0 | +1 |
| IL-12 p70 | 0 | 0 | +11 | 0 |
| IL-13 | 0 | 0 | −5 | 1 |
| IL-15 | 0 | 0 | 0 | 0 |
| IL-16 | 1 | 1 | 1 | 1 |
| IL-17 | 0 | 0 | −43 | −5 |
| IL-18 | 0 | 0 | 0 | 0 |
| IL-20 | 0 | 0 | 0 | 0 |
| IL-21 | 0 | x | 0 | x |
| IL-23 | +4 | +3 | +6 | 1 |
| IL-24 | 0 | 0 | 0 | 0 |
| IL-27 | 0 | 1 | 0 | 1 |
| IL-28 | 0 | 0 | 0 | 0 |
| IL-29 | 0 | 0 | 0 | 0 |
| IL-31 | 0 | 0 | 0 | 0 |
| IL-33 | 0 | 0 | 0 | 0 |
| IL-34 | 0 | 0 | 0 | 0 |
| IFN-gamma | 0 | 0 | +600 | +3000 |
| G-CSF | −1500 | +20 | 1 | 1 |
| GM-CSF | 0 | 0 | 0 | 1 |
| CD MARKERS | | | | |
| CD14 | +2 | +2 | +2 | +2 |
| CD23 | −22 | 1 | −850 | −3 |
| CD30 | 0 | 0 | 0 | 0 |
| CD40 | +2 | +2 | 1 | 1 |
| CD97 | −2 | 1 | −5 | −5 |
| CD152 (CTLA-4) | 1 | 0 | −2 | 0 |
| CD154 | 1 | x | +2 | x |
| CD163 | −2 | 1 | −2 | 1 |
| CD200 | 1 | 1 | −1 | 1 |
| CD223 (LAG3) | 0 | 0 | −3 | +3 |
| SELECTED CHEMOKINES AND PROTEINS | | | | |
| CXCL1 (GROa) | −7600 | −12 | −3400 | 1 |
| CXCL5 (ENA-78) | −6 | +16 | −32 | −3 |
| CXCL10 (IP10) | +460 | +10 | +1 | 1 |
| CCL1 (1-309) | 0 | 1 | −24 | 1 |
| CCL7 (MCP-3) | −2 | −200 | −149 | 1 |
| CCL16 (HCC-4) | 0 | 1 | −100 | 1 |
| CCL20 (MIP-3a) | −69 | +40 | −2 | 1 |
| MMP-2 (collagenase) | +600 | +200 | +450 | +500 |
| MMP-10 (proteoglycanase) | −121 | 1 | −2 | −2 |
| ACE-2 | +12 | 0 | +6 | 0 |
| PDGF Ralpha | −4 | −7 | −1 | −3 |
| Tie-1 | −170 | −200 | −8 | −280 |
| ICAM-1 | −1 | +2 | −3 | 1 |
| TREM-1 | +5 | −2 | +2 | −5 |
| E-SELECTIN | 1 | −7 | 1 | −2 |

0 = no analyte detected

1 = analyte present but no effect of alpha-10/14 x = not determined

The positive effect of alpha-10/14 is denoted by a +

The negative effect of alpha-10/14 interferon is denoted by a −

*The assay system used was the RayBio Quantibody Human Cytokine Array 9000 (QAH-CAA-9000 provided by Insight Bio Ltd.). This a multiplex ELISA, measuring the concentrations of 400 proteins in a single assay process, including pro- and anti-inflammatory markers, interleukins, cancer markers, chemokines, growth factors and related molecules. Human peripheral blood mononuclear leukocytes (normal blood donors) were treated with 10 ng/ml IFN-α14/10 for 4 hours prior to assay.

Tests were performed on 2 groups of cells - a) unactivated and b) activated with PHA (phytohaemagglutinin) to induce a high level of stimulation.

Effects of Alpha-14 on Activated Immune Cells

More than 30 interleukins were quantitated but only 6 showed significant changes in the activated cells, indicating the targeted and very specific nature of the interaction of the alpha-14 with the human immune response.

Interleukin 2 increased by 7-fold, IL-12p70 +11 fold and interferon-γ+600 fold, indicating a strong proliferation of the Th1 (cell-mediated) response while a 6-fold increase in IL-23 is in keeping with its role in cell-mediated immunity and its association with IL-12.

Very large decreases were observed with IL-3 and IL-5 of 11 and 420-fold respectively. These molecules are associated with the production of myeloid cells and immunoglobulin production (humoral immunity). IL13 also decreased by 5-fold, which is important as this interleukin is implicated in the secretion of IgE, the allergy antibody. Also crucial was the 43-fold decrease in IL-17. This regulatory cytokine is increased in autoimmune diseases, humoral (antibody-mediated) immunity and stimulation of inflammation through attraction of neutrophils.

CD23 or FcεRII is a receptor for the allergy antibody, IgE, and is displayed widely on different types of leukocytes. CD23 activation controls IgE production and significant increases are seen in patients with allergic disorders. This important marker was decreased by 850-fold, in the activated cells, by alpha-14.

Effects of IFN Alpha-14 on Non-Activated Immune Cells

IL-6 decreased 19-fold. This cytokine stimulates liver protein synthesis in responses to traumas, causes increases in body temperature and is involved in muscle contraction. However, it is its essential role in antibody-mediated immunity that is important in allergy.

G-CSF was also decreased by more than 1000-fold. This molecule can stimulate the bone marrow to make Increased numbers of neutrophils that could be involved in inflammation. At the same time the secretion of the chemokine CXCL1 was suppressed by 7,500-fold—this prevents it attracting neutrophils to the site of a response and causing inflammation. Also the concentration of the chemokine, CXCL10 was enhanced by 460-fold—its role is to attract T-lymphocytes to an ongoing immune response.

Effects of IFN Alpha-10 on Activated Immune Cells

As with alpha-14, alpha-10 only regulated a small number of cytokines out of the numbers assessed. Of particular note were the increases in IL-2 and interferon-γ of 4 and 3000 fold respectively indicating a switch to cell-mediated immunity. IL-17 levels fell by 5 fold, confirming this change in balance.

The large reduction in CD23 was not evident with alpha-10 and its major effects on chemokines were on Tie-1 (tyrosine kinase crucial in the process of lymphatic remodelling) and TREM-1 (neutrophil activation) where it caused reductions of 280 and 5 fold respectively.

Effects of Alpha-10 on Non-Activated Immune Cells

Alpha-10 showed significant activity in this context enhancing IL-1α/β by up to 70fold and IL-6,8,10,12 (p40) by 1000,100, 5 and 350 fold in keeping with a strong support for cell-mediated over humoral immunity. G-CSF was also enhanced by 20 fold in total contrast to alpha-14.

Few changes were recorded with the CD markers but CXCL1 was reduced by 12 fold while CXCL5 and 10 increased by 16 and 10 fold and CCL20 rose by 40 fold. However, CCL7 and Tie-1 fell by 200 fold each. These results are in keeping with a significant movement towards cell-mediated immunity.

RESULT

The low doses of interferon-alpha 14 and 10 have modified cytokine synthesis in order to enhance cell-mediated immunity at the expense of antibody-mediated immunity. This would be invaluable in enhancing the activities of certain vaccines where a humoral immune response can be detrimental e.g. viral and cancer vaccines.

In addition the results are totally in keeping with the general understanding that allergy can be alleviated by changing the immune response to an allergen by shifting an antibody response to a cellular response. Such a change would be part of acquired immunity and hence, potentially, a long-term solution by developing tolerance.

In addition, the alpha-14 significantly suppressed the capacity of leukocytes to make/utilise IgE and hence it inhibited the immediate effects of an allergic reaction, together with reducing inflammatory elements of immunity while enhancing the involvement of more control elements.

All documents referred to in this specification are herein incorporated by reference.

Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

What is claimed is:

1. A method for enhancing a Th1l-mediated immune response and suppressing a Th2/Th17-mediated immune response in a subject, said method comprising the step of:
   (i) administering to the subject a therapeutically effective amount of a IFN-α10-IFN-α14 hybrid, wherein the IFN-α10-IFN-α14 hybrid comprises the amino acid sequence set forth by SEQ ID NO: 1.

2. The method as claimed in claim 1, wherein the subject suffers from a condition selected from the group consisting of: an autoimmune disease, an inflammatory disease, an allergy, an allergic disease, and a cancer.

3. The method as claimed in claim 2, wherein the inflammatory disease is inflammatory bowel disease, ulcerative colitis, or Crohn's disease.

4. The method as claimed in claim 2, wherein the allergy or the allergic disease is a food allergy.

5. The method as claimed in claim 2, wherein the method further comprises administering to the subject a therapeutically effective amount of a vaccine composition for treatment of the condition.

6. The method as claimed in claim 5, wherein the vaccine composition comprises at least one allergen capable of mediating a Th2/Th17 immune response, a food allergen capable of mediating a Th2/Th17 immune response, or a tumour antigen capable of mediating a Th2/Th17 immune response.

7. The method as claimed in claim 1, wherein the IFN-α10-IFN-α14 hybrid has improved binding to interferon receptor 1 and interferon receptor 2 in comparison to IFN-α10 or IFN-α14.

8. A method for suppressing IL-17 expression in a subject having a condition mediated by enhanced expression of IL-17, said method comprising the step of:
   (i) administering to the subject a therapeutically effective amount of a IFN-α10-IFN-α14 hybrid, wherein the IFN-α10-IFN-α14 hybrid comprises the amino acid sequence set forth by SEQ ID NO: 1.

9. The method as claimed in claim 8, wherein the IFN-α10-IFN-α14 hybrid has improved binding to interferon receptor 1 and interferon receptor 2 in comparison to IFN-α10 or IFN-α14.

10. The method of claim 6, wherein the tumour antigen is a tumour specific antigen or tumour-associated antigen.

11. The method as claimed in claim 2, wherein the cancer is hepatic cell cancer, lung cancer, non-small cell lung cancer, ovarian cancer, breast cancer, skin cancer, melanoma, genitourinary cancer, prostate cancer, renal cell cancer, or bladder cancer.

12. The method of claim 2, wherein the allergy is selected from the group consisting of: a food allergy, an environmental allergy, Heiner syndrome, oral allergy syndrome, eosinophilic gastroenteritis, IgE mediated gastrointestinal food allergy, and C1 esterase deficiency.

* * * * *

UNITED STATES PATENT AND TRADEMARK OFFICE
CERTIFICATE OF CORRECTION

PATENT NO. : 11,267,860 B2
APPLICATION NO. : 15/760200
DATED : March 8, 2022
INVENTOR(S) : Stimson It is certified that error appears in the above-identified patent and that said Letters Patent is hereby corrected as shown below:

In the Claims

Column 37,
Line 29, "Th11-mediated" should read --Th1-mediated--.

Signed and Sealed this
Twenty-first Day of February, 2023

Katherine Kelly Vidal
*Director of the United States Patent and Trademark Office*